US 9,522,348 B2

(12) United States Patent
Lynn

(10) Patent No.: US 9,522,348 B2
(45) Date of Patent: *Dec. 20, 2016

(54) OZONATED LIQUID DISPENSING UNIT

(71) Applicant: Food Safety Technology, LLC, Omaha, NE (US)

(72) Inventor: Daniel W. Lynn, Omaha, NE (US)

(73) Assignee: FOOD SAFETY TECHNOLOGY, LLC, Omaha, NE (US)

( * ) Notice: Subject to any disclaimer, the term of this patent is extended or adjusted under 35 U.S.C. 154(b) by 538 days.

This patent is subject to a terminal disclaimer.

(21) Appl. No.: 13/743,945

(22) Filed: Jan. 17, 2013

(65) Prior Publication Data

US 2013/0142704 A1    Jun. 6, 2013

Related U.S. Application Data

(63) Continuation-in-part of application No. 12/816,837, filed on Jun. 16, 2010, now Pat. No. 9,174,845, which
(Continued)

(51) Int. Cl.
*B01D 19/02* (2006.01)
*A23B 7/157* (2006.01)
(Continued)

(52) U.S. Cl.
CPC ............. *B01D 19/02* (2013.01); *A23B 7/157* (2013.01); *A23B 7/158* (2013.01); *A23L 1/0011* (2013.01);
(Continued)

(58) Field of Classification Search
CPC ............. A61L 2/18; A61L 2/183; A61L 2/26; B01D 19/02; C01B 13/11; C11D 3/2093; C11D 3/38636; C11D 3/50; C11D 3/39; A23L 5/57; A23L 7/157; A23L 7/158
See application file for complete search history.

(56) References Cited

U.S. PATENT DOCUMENTS 3,298,314 A    1/1967   Kopczynski
3,549,134 A   12/1970   Kapacheva et al.
(Continued)

FOREIGN PATENT DOCUMENTS

CA        2491781         7/2005
DE    202 0050 11195 U1   1/2006
(Continued)

OTHER PUBLICATIONS

Office Action for U.S. Appl. No. 12/179,335 dated Nov. 23, 2011 (12 pages).
(Continued)

*Primary Examiner* — Reginia M Yoo
(74) *Attorney, Agent, or Firm* — Polsinelli PC

(57) ABSTRACT

A reaction vessel and an ozonated liquid dispensing unit are described herein. The unit produces and dispenses an ozonated liquid that may be used to clean and sanitize a variety of articles or used in conjunction with cleaning processes and other apparatus. The reaction vessel is incorporated into the unit to reduce bubbles of ozone gas and to break up bubbles of ozone gas in the ozonated liquid to provide a more effective and longer lasting cleaning and sanitizing solution.

23 Claims, 12 Drawing Sheets

Related U.S. Application Data is a continuation-in-part of application No. 12/179,335, filed on Jul. 24, 2008, now abandoned.

(51) Int. Cl.

| | | |
|---|---|---|
| *A23B 7/158* | (2006.01) | |
| *C01B 13/11* | (2006.01) | |
| *C11D 3/39* | (2006.01) | |
| *C11D 3/50* | (2006.01) | |
| *A23L 1/00* | (2006.01) | |
| *C11D 3/20* | (2006.01) | |
| *C11D 3/386* | (2006.01) | |
| *A61L 2/18* | (2006.01) | |

(52) U.S. Cl.
CPC ................. *A23L 5/57* (2016.08); *A61L 2/183* (2013.01); *C01B 13/11* (2013.01); *C11D 3/2093* (2013.01); *C11D 3/38636* (2013.01); *C11D 3/39* (2013.01); *C11D 3/50* (2013.01); *A23V 2002/00* (2013.01); *A61L 2/18* (2013.01); *C01B 2201/32* (2013.01); *C01B 2201/40* (2013.01); *C01B 2201/62* (2013.01); *C01B 2201/64* (2013.01)

(56) References Cited

U.S. PATENT DOCUMENTS

| | | |
|---|---|---|
| 4,035,657 A | 7/1977 | Carlson |
| 4,049,552 A | 9/1977 | Arff |
| 4,123,800 A | 10/1978 | Mazzei |
| 4,138,330 A | 2/1979 | Garrett |
| 4,176,061 A | 11/1979 | Stopka |
| 4,352,740 A | 10/1982 | Grader et al. |
| 4,517,159 A | 5/1985 | Karlson |
| 4,555,335 A | 11/1985 | Burris |
| 4,650,573 A | 3/1987 | Nathanson |
| 4,686,036 A | 8/1987 | Laederach-Zaugg |
| 4,801,310 A | 1/1989 | Bielefeldt |
| 4,834,343 A | 5/1989 | Boyes |
| 4,849,237 A | 7/1989 | Hurst |
| 4,900,481 A | 2/1990 | Kishioka |
| 4,963,269 A | 10/1990 | Sasaki et al. |
| 5,005,364 A | 4/1991 | Nelson |
| 5,069,880 A | 12/1991 | Karlson |
| 5,174,905 A | 12/1992 | Shawn |
| 5,186,841 A | 2/1993 | Schick |
| 5,207,237 A | 5/1993 | Langford |
| 5,213,773 A | 5/1993 | Burris |
| 5,236,512 A | 8/1993 | Rogers et al. |
| 5,411,713 A | 5/1995 | Iwanaga |
| 5,493,754 A | 2/1996 | Gurstein et al. |
| 5,514,267 A | 5/1996 | Machiya |
| 5,556,200 A | 9/1996 | Ekholm et al. |
| 5,641,456 A | 6/1997 | Rosenauer |
| 5,645,797 A | 7/1997 | Lo |
| 5,670,094 A | 9/1997 | Sasaki et al. |
| 5,720,905 A | 2/1998 | Ho |
| 5,815,869 A | 10/1998 | Hopkins |
| 5,824,243 A | 10/1998 | Contreras |
| 5,824,274 A | 10/1998 | Long |
| 5,839,155 A | 11/1998 | Berglund et al. |
| 5,855,856 A | 1/1999 | Karlson |
| 5,863,128 A | 1/1999 | Mazzei |
| 5,865,995 A | 2/1999 | Nelson |
| 5,914,089 A | 6/1999 | Murakami et al. |
| 5,951,511 A | 9/1999 | Lowder |
| 5,951,921 A | 9/1999 | Koganezawa et al. |
| 6,030,586 A | 2/2000 | Kuan |
| 6,039,815 A | 3/2000 | Yeol et al. |
| 6,076,808 A | 6/2000 | Porter |
| 6,106,731 A | 8/2000 | Hayes |
| 6,115,862 A | 9/2000 | Cooper et al. |
| 6,132,629 A | 10/2000 | Boley |
| 6,139,809 A * | 10/2000 | Rodden .................... C01B 13/11 422/186.07 |
| 6,153,151 A | 11/2000 | Moxley et al. |
| 6,197,206 B1 | 3/2001 | Wasinger |
| 6,200,014 B1 | 3/2001 | Babenko |
| 6,207,064 B1 | 3/2001 | Gargas |
| 6,250,324 B1 | 6/2001 | Conrad et al. |
| 6,254,838 B1 | 7/2001 | Goede |
| 6,270,733 B1 * | 8/2001 | Rodden .................... C01B 13/11 204/176 |
| 6,274,053 B1 | 8/2001 | Conrad |
| 6,276,304 B1 | 8/2001 | Tai |
| 6,315,887 B1 | 11/2001 | Salama |
| 6,348,227 B1 | 2/2002 | Caracciolo |
| 6,361,688 B1 | 3/2002 | Nelson |
| 6,402,855 B1 | 6/2002 | Damron et al. |
| 6,455,017 B1 | 9/2002 | Kasting, Jr. et al. |
| 6,458,257 B1 | 10/2002 | Andrews et al. |
| 6,458,398 B1 | 10/2002 | Smith et al. |
| 6,464,210 B1 | 10/2002 | Teran et al. |
| 6,499,671 B1 | 12/2002 | Sands et al. |
| 6,517,731 B2 | 2/2003 | Conrad |
| 6,585,898 B1 | 7/2003 | Ekberg et al. |
| 6,638,364 B2 | 10/2003 | Harkins et al. |
| 6,649,052 B2 | 11/2003 | Lee et al. |
| 6,723,999 B2 * | 4/2004 | Holl .............................. 250/438 |
| 6,755,977 B2 | 6/2004 | Brunsell |
| 6,808,637 B2 | 10/2004 | Cho |
| 6,817,541 B2 | 11/2004 | Sands et al. |
| 6,837,944 B2 | 1/2005 | Kashkoush et al. |
| 6,886,373 B2 | 5/2005 | Carrubba et al. |
| 6,948,504 B2 | 9/2005 | Fittkau et al. |
| 6,962,654 B2 | 11/2005 | Arnaud |
| 6,964,739 B2 | 11/2005 | Boyd et al. |
| 6,982,006 B1 | 1/2006 | Boyers et al. |
| 6,991,685 B2 | 1/2006 | Kravitz et al. |
| 7,001,571 B2 * | 2/2006 | Forney et al. .................. 422/22 |
| 7,022,225 B1 | 4/2006 | Clawson et al. |
| 7,086,407 B2 | 8/2006 | Lynn |
| 7,087,123 B2 | 8/2006 | Lynn |
| 7,087,124 B2 | 8/2006 | Lynn |
| 7,108,781 B2 | 9/2006 | Martin |
| 7,188,632 B2 | 3/2007 | Lynn |
| 7,255,332 B2 | 8/2007 | Osborn et al. |
| 7,264,006 B2 | 9/2007 | Fittkau et al. |
| 7,264,680 B2 | 9/2007 | Gebhart et al. |
| 7,272,947 B2 | 9/2007 | Anderson et al. |
| 7,275,982 B1 | 10/2007 | Brandt et al. |
| 7,276,168 B2 | 10/2007 | Hibara et al. |
| 7,425,301 B2 | 9/2008 | Gillette et al. |
| 7,507,370 B2 * | 3/2009 | Forney et al. .................. 422/24 |
| 8,071,526 B2 | 12/2011 | Lynn |
| 8,080,165 B2 * | 12/2011 | Forney .................... 210/748.11 |
| 8,636,634 B2 * | 1/2014 | Allen et al. ........................ 494/2 |
| 2001/0030295 A1 * | 10/2001 | Holl .......................... 250/492.23 |
| 2002/0190404 A1 | 12/2002 | Baarda |
| 2003/0049164 A1 | 3/2003 | Bon et al. |
| 2003/0156978 A1 | 8/2003 | Gillete et al. |
| 2004/0025750 A1 * | 2/2004 | Stalder et al. ................. 106/499 |
| 2004/0074252 A1 | 4/2004 | Shelton |
| 2004/0126273 A1 * | 7/2004 | Forney et al. .................. 422/22 |
| 2004/0154641 A1 | 8/2004 | Montierth |
| 2005/0103725 A1 | 5/2005 | Palm et al. |
| 2005/0167369 A1 | 8/2005 | Robinson et al. |
| 2005/0214159 A1 | 9/2005 | Schwei et al. |
| 2006/0175263 A1 | 8/2006 | Rice et al. |
| 2007/0086913 A1 | 4/2007 | Teran et al. |
| 2007/0199581 A1 | 8/2007 | Lynn et al. |
| 2007/0205161 A1 | 9/2007 | Chiba et al. |
| 2008/0227680 A1 | 9/2008 | Lynn |
| 2009/0008806 A1 | 1/2009 | Lynn |
| 2009/0032473 A1 | 2/2009 | Ueki et al. |
| 2009/0081340 A1 * | 3/2009 | Forney ........................... 426/248 |
| 2009/0120473 A1 | 5/2009 | Lynn |
| 2009/0233839 A1 | 9/2009 | Lynn |
| 2010/0010422 A1 | 1/2010 | Watanabe |
| 2010/0021598 A1 | 1/2010 | Lynn |
| 2010/0175311 A1 * | 7/2010 | Allen et al. ........................ 44/403 |
| 2010/0252415 A1 | 10/2010 | Lynn |

(56) References Cited

U.S. PATENT DOCUMENTS

FOREIGN PATENT DOCUMENTS

| | | |
|---|---|---|
| GB | 2 144 610 A | 3/1985 |
| JP | 52-125466 | 10/1977 |
| JP | H06-039232 A | 2/1994 |
| JP | 2003-320232 | 11/2003 |
| JP | 2004-066050 A | 3/2004 |
| JP | 2004-330050 A | 11/2004 |
| JP | 2005-021869 A | 1/2005 |
| JP | 2005-144320 A | 6/2005 |
| JP | 2005-334797 A | 12/2005 |
| JP | 2008-012415 A | 1/2008 |
| JP | 2008-524530 A | 7/2008 |
| JP | 2009-142750 A | 9/2008 |
| JP | 2009-274026 A | 11/2009 |
| JP | H10-034173 A | 2/2010 |
| RU | 2 177 456 C2 | 1/2000 |
| SU | 1049091 A | 10/1983 |
| WO | 01-72432 A1 | 10/2001 |
| WO | 2003-084652 A2 | 10/2003 |
| WO | 2008-112947 A1 | 9/2008 |
| WO | 2010-047167 A | 4/2010 |

OTHER PUBLICATIONS

Office Action for U.S. Appl. No. 12/816,837 dated Sep. 25, 2012 (12 pages).
Office Action for U.S. Appl. No. 12/468,952 dated Nov. 25, 2011 (17 pages).
Office Action for U.S. Appl. No. 12/047,498 dated Aug. 31, 2010 (13 pages).
Office Action for U.S. Appl. No. 12/047,461 dated May 21, 2010 (12 pages).
Office Action for U.S. Appl. No. 12/047,442 dated May 12, 2010 (15 pages).
Office Action for U.S. Appl. No. 12/047,442 dated Jan. 10, 2011 (20 pages).
International Search Report and Written Opinion dated Sep. 1, 2009 for PCT/US09/51636 (7 pages).
International Search Report and Written Opinion dated Dec. 2, 2011 for PCT/US2011/039756 (11 pages).
International Search Report and Written Opinion dated Oct. 5, 2011 for PCT/US2011/039711 (9 pages).
International Search Report and Written Opinion dated Jun. 3, 2008 for PCT/US08/56936 (13 pages).
Suslow; "Oxidation Reduction Potential (ORP) for Water Disinfection Monitoring, Control and Documentation"; University of California, Division of Agriculture and Natural Resources, 2004 (5 pages).
Office Action for U.S. Appl. No. 12/179,335 mailed Jun. 7, 2012 (11 pages).
Office Action for U.S. Appl. No. 12/179,335 mailed Sep. 26, 2013 (13 pages).
Office Action for U.S. Appl. No. 12/179,335 mailed May 16, 2014 (11 pages).
AU Appl. No. 2011267991 Examination Report dated Jun. 7, 2013 (4 pages).
Office Action for U.S. Appl. No. 12/468,952 dated May 9, 2013 (6 pages).
Office Action for U.S. Appl. No. 12/047,442 dated Dec. 16, 2013 (24 pages).
Office Action for U.S. Appl. No. 12/047,442 dated Oct. 16, 2014 (24 pages).

\* cited by examiner

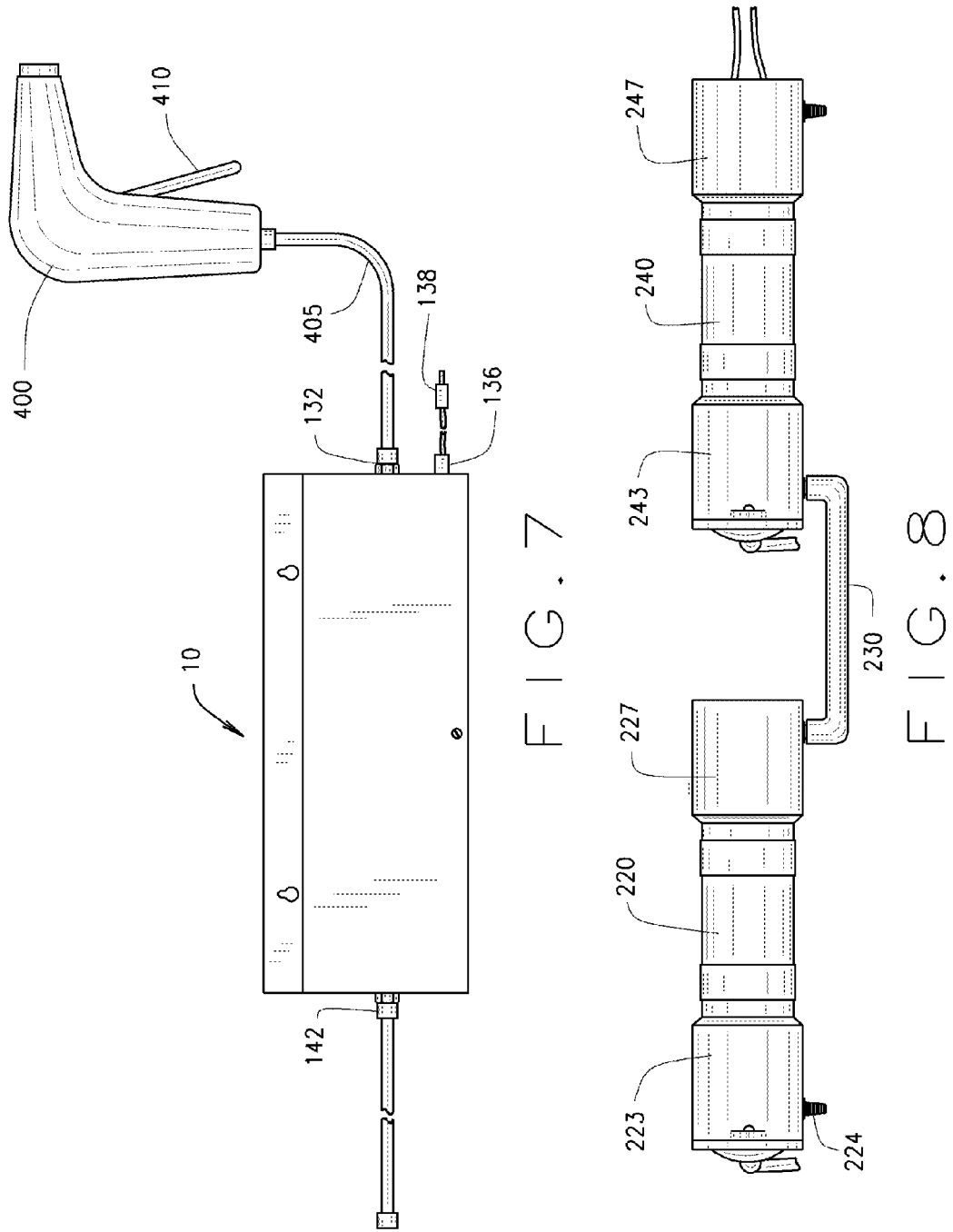

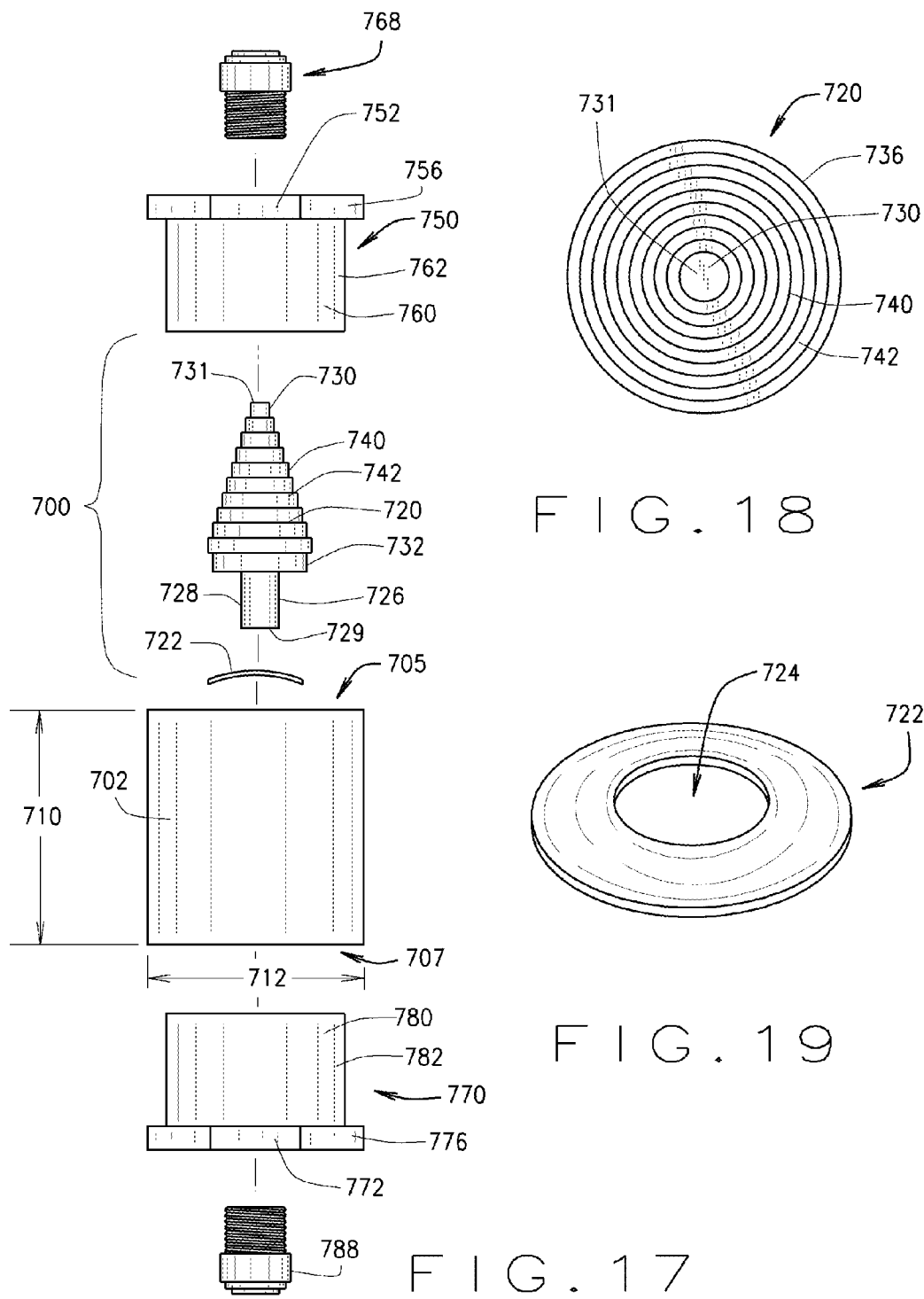

OZONATED LIQUID DISPENSING UNIT

CROSS REFERENCE TO RELATED APPLICATION

This application is a continuation-in-part of U.S. Nonprovisional patent application Ser. No. 12/816,837 filed Jun. 16, 2010, which is a continuation-in-part of U.S. Nonprovisional patent application Ser. No. 12/179,335 filed Jul. 24, 2008, which are both hereby incorporated by reference.

FIELD OF INVENTION

The present invention relates to an ozonated liquid dispensing unit that produces and dispenses an ozonated liquid that may be used to clean and sanitize a variety of articles or used in conjunction with cleaning processes and other apparatus, and the present invention further relates to a reaction vessel that may be used with the ozonated liquid dispensing unit.

BACKGROUND OF INVENTION

Prior attempts to provide an ozonated liquid in a kitchen environment have failed to provide an ozonated liquid with sufficient concentrations of ozone resulting in poor cleaning and sanitizing. Without sufficient ozone concentration, conventional cleaning and sanitizing methods may still be necessary at extra labor, equipment, and supply costs.

Other prior attempts to provide an ozonated liquid have involved electrochemical ozone generation. Such systems are difficult to maintain. Such systems are often too large and too bulky to be effectively used in some residential or commercial applications. Many of these systems are also too expensive for use in the home or are not economical to be used in commercial applications. Such systems often require significant mechanical alterations to existing water supply and delivery systems. Such systems also require the output of ozone gas to be adjusted each time the system is turned on. Further, many previous systems cannot be used with multiple, different dispensing applications.

Other prior attempts to provide an ozonated liquid have involved systems that create too much off-gassing of ozone. Although ozone gas is generally harmless, OSHA workplace requirements require that ozone levels are maintained below certain minimums.

SUMMARY OF INVENTION

A reaction vessel and an ozonated liquid dispensing unit are described herein. The unit produces and dispenses an ozonated liquid that may be used to clean and sanitize a variety of articles or used in conjunction with cleaning processes and other apparatus. The reaction vessel is incorporated into the unit to reduce bubbles of ozone gas and to break up bubbles of ozone gas in the ozonated liquid to provide a more effective and longer lasting cleaning and sanitizing solution.

The reaction vessel passes the ozonated liquid against and past a contact member that helps break up the bubbles. In one aspect, the contact member includes a cone. The reaction vessel provides a more uniform size distribution of the bubbles of ozone gas in the ozonated liquid, which assists in maintaining the oxidation reduction potential of the solution.

The ozonated liquid dispensing unit is compact, may be conveniently installed in a commercial or residential kitchen, restroom or other area with a water supply. The units provides an ozonated liquid with a high concentration of ozone gas sufficient to clean and sanitize food items, food preparation items, food preparation surface, bathrooms, medical equipment, drains and to provide for hand-washing and hygiene needs. The unit uses multiple dielectric cells in an in-line configuration to create the ozone gas that is mixed with the water to form the ozonated liquid. A first dielectric cell prepares ozone gas that is supplied to a second dielectric cell, which creates additional ozone gas, thus creating a highly concentrated supply of ozone gas that is supplied to an injector.

Foods, food preparation areas, as well as other surfaces, may benefit from sterilization provided by the unit. In the food industry, the ozonated liquid from the unit provides for chemical-free sterilization of contaminated surfaces and tools, such as those used in the processing of raw meat. The ozonated liquid cleans toxic substances 3,000 times faster than chlorine, and unlike chlorine, ozonated liquid is completely safe and natural. The ozonated liquid is a bactericidal, fungicidal, and virucidal and kills micro-organisms, including *e. coli*, salmonella, bacteria, viruses, molds, etc. The ozonated liquid also remove pesticides and other residues from fruits and vegetables. The ozonated liquid also reduces odors in the environment on which the ozonated liquid is sprayed. The unit is ideal for residential food preparation, commercial food preparation, or any place a sterile, cleaning solution is needed. In a commercial setting, fruits and vegetables, may be washed with the unit and its ozonated liquid to increase the shelf-life of the items. By removing the micro-organisms from the surfaces of the fruit and vegetables that may cause decay and spoilage, the fruit and vegetables will not decay or spoil as fast. The workers may also wash their hands with the ozonated liquid from the unit, The ozonated liquid dispensing unit includes a liquid input port to receive the liquid, such as water, into the unit to be mixed with ozone gas to form the ozonated liquid. The unit includes the first dielectric cell for producing ozone gas from ambient air and the second dielectric cell for producing ozone gas. The first dielectric cell is in supply communication with the second dielectric cell for supplying the second dielectric cell with a supply gas comprising the ozone gas generated from the ambient air. The second dielectric cell produces ozone gas from the supply gas. The injector is in fluidic communication with the liquid input port. The injector in supply communication with the second dielectric cell for receiving the ozone gas from the second dielectric cell, and the injector mixes the ozone gas from the second dielectric cell with the liquid from the liquid input port to produce an ozonated liquid. A liquid output port discharges the ozonated liquid from the unit. A faucet or spray may be used to control the discharge of the ozonated liquid from the unit.

The unit is easy to install. Generally, the unit is just plugged into an electrical unit and a water supply is provided to the unit. The unit discharges the ozonated liquid into a liquid supply line in fluidic communication with a sprayer or faucet. A handle, knob or other actuator is manipulated in order to begin the production and flow of ozonated liquid from the unit.

In other aspects, an ozonated liquid dispensing unit is provided. The ozonated liquid dispensing unit incorporates the reaction vessel. The unit uses multiple dielectric cells in an in-line configuration to create ozone gas from the oxygen gas. The ozone gas is injected into water or fluid to form the ozonated liquid. Ozone gas is unstable, which provides for it cleaning and sanitizing capabilities, but also makes consistent ozone levels difficult to maintain when the gas is mixed into a solution. Ozone gas cannot be packaged or stored and must be generated on site. The unit reduces the need for chemicals, hot water, and labor. Conventional cleaning systems often require the use of warm or hot water, which may form condensation in the surrounding workspace. This condensation may provide for or encourage the growth of microorganisms, as well as promoting cross-contamination. Because unit only uses cold water, condensation is less likely to form in the surrounding workspace. The unit also reduces the hydraulic load on the waste-water treatment system and eliminates the need to treat the chemicals that would be present in conventional wastewater discharge streams.

In other aspects, a reaction vessel for processing an ozonated fluid is provided. The reaction vessel reduces a bubble size of ozone gas bubbles in the ozonated fluid. The reaction vessel includes a housing. The housing includes an entry port and an exit port. The housing defines an interior. The reaction vessel further includes a contact member. The contact member includes a contact surface. The contact member is positioned in the interior of the housing. An annular fluid passage is formed between the contact surface and an inner surface of the housing. The annular fluid passage fluidly connects the entry port and the exit port with the interior. The reaction vessel processes the ozonated fluid to reduce the bubble size of the ozone gas in the ozonated fluid and to reduce the number of ozone gas bubbles in the ozonated fluid to increase the concentration of ozone in the ozonated fluid.

In other aspects, the reaction vessel includes a housing. The housing defines an interior. The reaction vessel includes a first end. The first end includes an entry port for an ozonated fluid. The reaction vessel includes a second end. The second end includes an exit port for the ozonated fluid. The reaction vessel includes a cone positioned in the interior of the housing between the entry port and the exit port. The cone includes a first cone end and a second cone end. The first cone end has a smaller external diameter than the second end. The entry port directs the ozonated fluid toward the first cone end.

In other aspects, the reaction vessel includes a housing. The housing has a generally cylindrical shape. The housing defines an interior. The housing has a first opening and second opening. The reaction vessel includes a first end. The first end includes a first rim portion and a first insert portion. The first end also includes a first central opening that allows the ozonated fluid to enter the housing. The reaction vessel includes a second end. The second end includes a first rim portion and a first insert portion. The second end also has a second central opening that allows the ozonated fluid to exit from the housing. The first insert portion fits into the first opening of the housing to connect the first end to the housing. The second insert portion fits into the second opening of the housing to connect the second end to the housing. A cone is positioned in the interior of the housing. The cone is held in place by the first end and the second end.

In other aspects, a method to reduce a bubble size of ozone gas bubbles in an ozonated solution is described. The method includes providing a reaction vessel. The reaction vessel includes a housing. The housing defines an interior. The reaction vessel includes a first end that includes an entry port for an ozonated fluid. The reaction vessel includes a second end that includes an exit port for the ozonated fluid. The cone is positioned in the interior of the housing between the entry port and the exit port. The cone includes a first cone end and a second cone end. The first cone end has a smaller external diameter than the second end. The entry port directs the ozonated fluid toward the first cone end. The method further includes directing an ozonated fluid to an entry port of the reaction vessel. The method further includes directing an ozonated fluid against or around the cone to reduce a bubble size of ozone gas bubbles in the ozonated solution.

Ozone creates none of the trihalomethanes commonly associated with chlorine compounds. When properly matched to the application, ozone will reduce most organic compounds to carbon dioxide, water and a little heat. Finally, as ozone sheds the atom of the oxygen causing its molecular instability during the oxidation process, it becomes oxygen again.

DESCRIPTION OF FIGURES

FIG. 7 is a view showing a sprayer attached to the ozonated liquid dispensing unit.

FIG. 8 is a view of the first and second dielectric cells.

FIG. 17 is an exploded view of the reaction vessel.

FIG. 18 is a view of the first end of the cone.

FIG. 19 is a perspective view of the spacer.

DETAILED DESCRIPTION OF INVENTION

Figure 1:
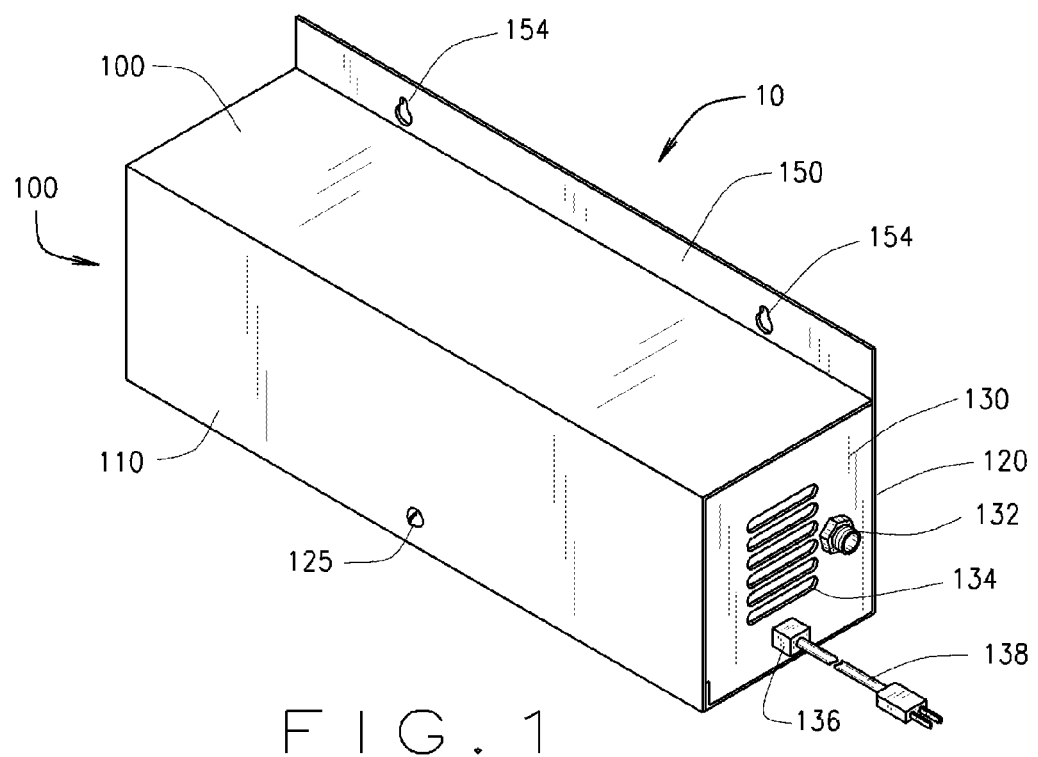
FIG. 1 shows a perspective view of the ozonated liquid dispensing unit with the output side of the unit visible.
Figure 2:
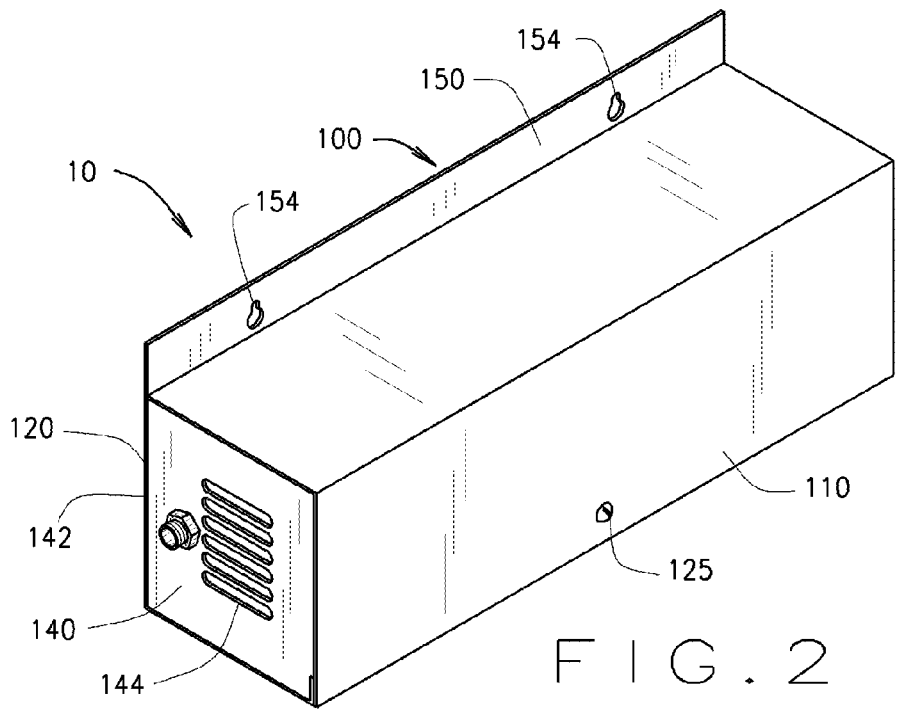
FIG. 2 is a perspective view of the ozonated liquid dispensing unit with the input side of the unit visible.

An ozonated liquid dispensing unit is described herein. With reference to FIGS. 1 and 2, an ozonated liquid dispensing unit 10 is shown. The unit 10 includes a housing 100, a removable housing cover 110 and a housing support 120. The housing 100, the housing cover 110, and the housing support 120 form a rectangular, box-like structure that houses the internal components of the unit 10. The housing 100 may be designed or engineered in other shapes and configurations. The housing 100, the housing cover 110, and the housing support 120 are made from sturdy or rugged materials, such as stainless steel, aluminum, or metals. Plastics and other composite materials may also be utilized in the construction of the housing 100, the housing cover 110 and the housing support 120.

Figure 4:
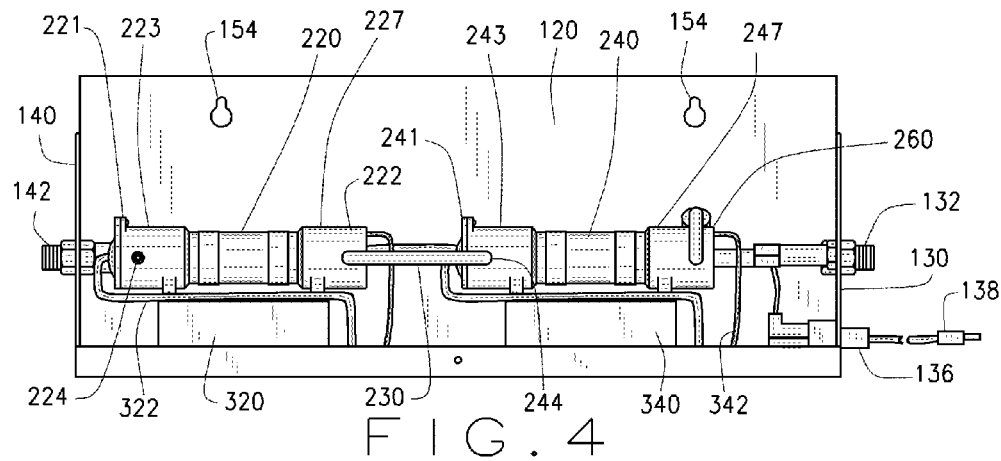
FIG. 4 is a front view of the ozonated liquid dispensing unit with the housing cover removed.
Figure 5:
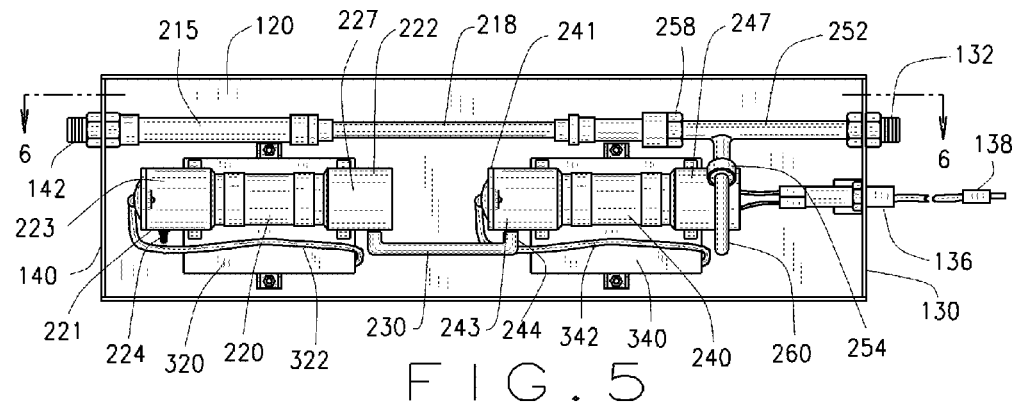
FIG. 5 is a top-down view of the ozonated liquid dispensing unit with the housing cover removed.
Figure 6:
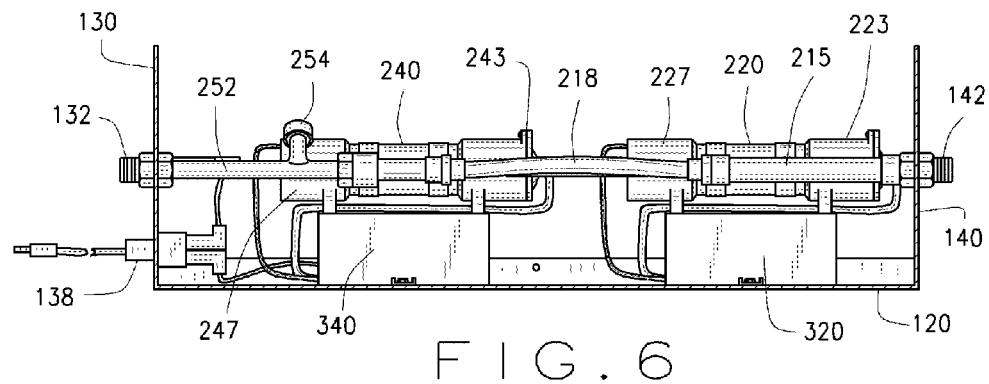
FIG. 6 is a rear view of the ozonated liquid dispensing unit with the housing cover removed.
Figure 9:
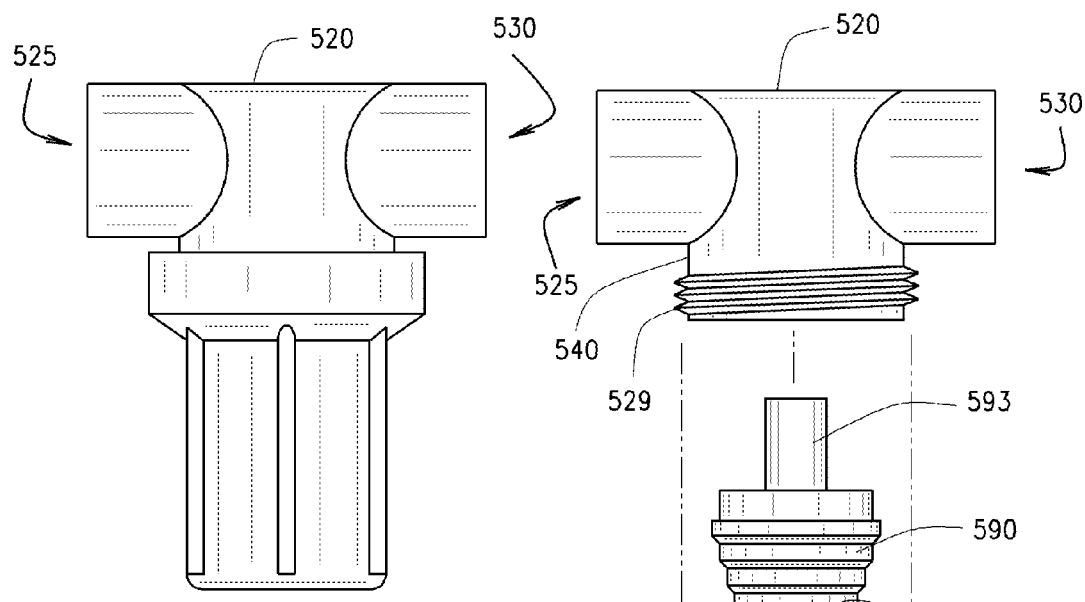
FIG. 9 is a side view of the reaction vessel.

As shown in FIGS. 4-6, the housing cover 110 is removed from the housing 100 to show the housing support 120, which receives and stabilizes the internal components of the unit 10. The housing cover 110 may be secured to the housing support 120 via securing means 125, such as a screw, pin, latch, lock, or other connection means for suitably attaching the housing cover 110 to the housing support 120 in a removable fashion.

FIG. 1 shows an output side 130 of the unit 10. The output side 130 includes a liquid output port 132 and an output side vent 134, and an electrical supply connection 136. The liquid output port 132 dispenses the ozonated liquid prepared in the unit 10 from the unit 10. The output side vent 134 assists in dissipating heat produced in the housing 100 from the electrical generation of ozone gas. The electrical supply connection 136 is in electrical communication with an electrical supply 138 to provide power to the unit 10.

FIG. 2 shows an input side 140 of the unit 10. The input side 140 is generally opposite of the output side 130. The input side 140 includes a liquid input port 142 and an input side vent 144. The liquid input port 142 includes threadable connections to receive a liquid input line 200 that supplies the unit 10 with water that is to be mixed with the ozone gas. The liquid input line 200 is threadably received by the liquid input port 142.

Ozonated liquid prepared by the unit 10 is discharged by the unit 10 from the liquid output port 132. A liquid output line 210 is connected to the liquid output port 132. The liquid output port 132 may include threadable connections for connecting the liquid output line 210 to the liquid output port 132. The liquid output line 210 supplies, for example, an ozone faucet 233 or other sprayer means, with a supply of the ozonated liquid.

Figure 3:
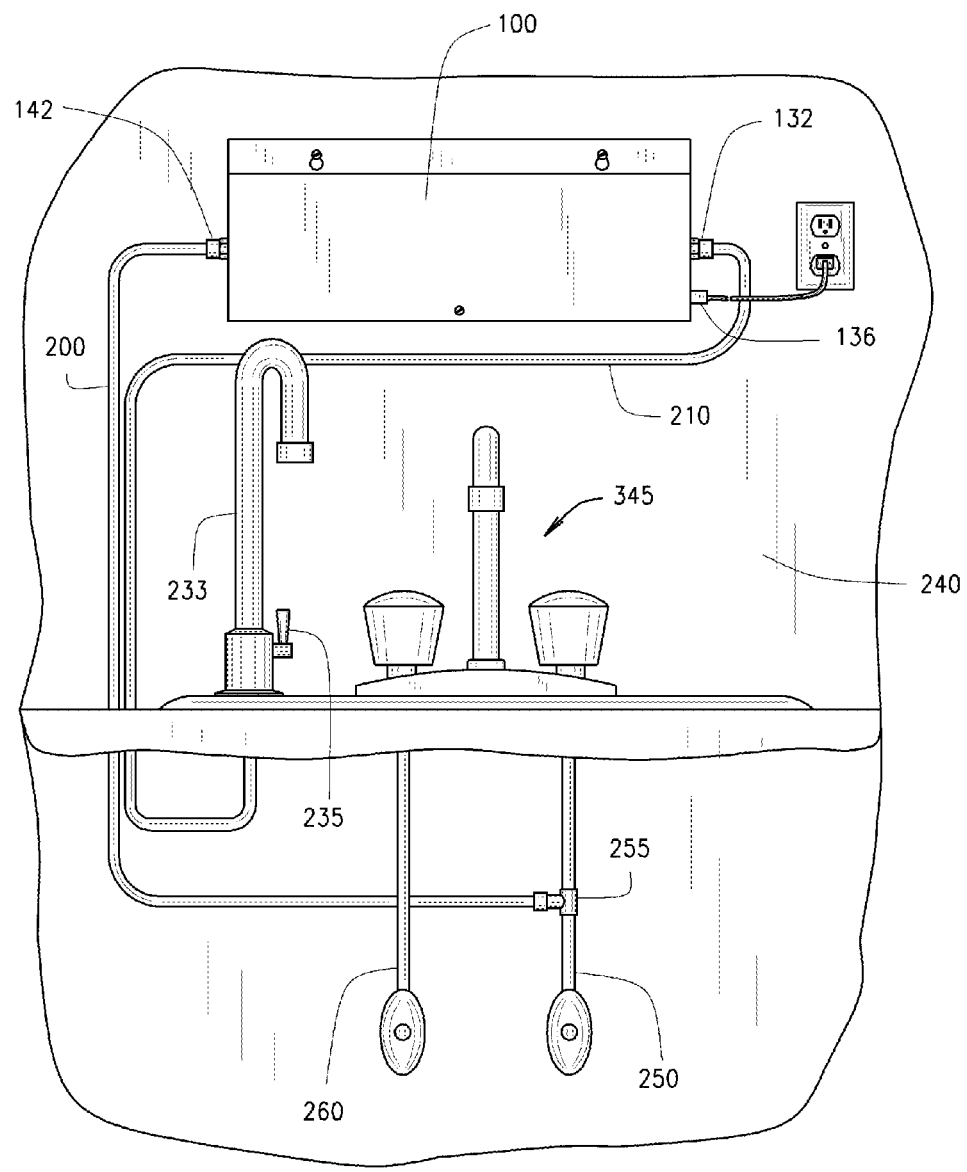
FIG. 3 is a plan diagram showing the installation of the ozonated liquid dispensing unit in conjunction with a sink and faucet.

The unit 10 may be conveniently mounted adjacent to or over a faucet/sink combination 345, such as shown in FIG. 3. The ozonated liquid may be disposed through the drain into existing waste water systems and the municipal sewer systems.

In the embodiments shown, the housing support 120 forms a flange 150 that extends beyond the housing cover 110. The flange 150 includes openings 154 which may be used to affix the unit 10 to a wall, cabinet or other structure via bolts, screws, rivets or other fastening means.

In other embodiments, the unit 10 may be placed onto a counter or underneath a counter in, for example, a kitchen cabinet or other storage area. FIG. 3 shows a diagram of unit 10 installed at the faucet/sink combination 345. During a typical installation of the unit 10, a t-shaped adaptor 255 is placed in the cold water supply 250. The adaptor 255 branches the cold water from the cold water supply 250 to the unit 10, while still providing normal cold water to the faucet/sink combination 345. The adapter 255 supplies fresh, cool water via the liquid input line 200 to the unit 10. The adapter 255 does not interrupt flow of the cool water supply 250 to the faucet/sink combination 345. A hot water supply 260 typically does not receive, or is involved with, the preparation of the ozonated liquid by the unit 10.

As ozone gas is created by the unit 10 and the ozone gas is mixed into the cold water entering the unit 10 from the cold water supply 250, the ozonated liquid is discharged at the liquid output port 132. The liquid output port 132 is in fluidic communication with an ozone faucet 233 via the liquid output line 210. By turning on a handle 235 of the ozone faucet 233, water is drawn into and through the unit 10 where ozonated gas prepared in the unit 10 is mixed with the water. During operation of the unit 10, the operator only needs to pull on the handle 235 in order for ozonated liquid to be discharged from the ozone faucet 233. The unit 10 does not require other manual actuation each time the unit 10 is used, i.e., the operator need not actuate an on/off switch or the like.

The internal components of the unit 10 are shown in FIGS. 4-6. Water from the cool water supply 250 enters a fluid flow switch 215, which activates the unit 10 upon sensing a flow of water. The fluid flow switch is in fluidic communication with an injector 252 via a liquid line 218.

The liquid line 218 fluidly connects the fluid flow switch 215 with the injector 252. The liquid line 218 may comprise a hose, plastic tubing, metal braided tubing, or other suitable structure for communicating liquid from the fluid flow switch 215 to the injector 252.

The water supplied to the injector 252 is mixed with ozone gas from the first dielectric cell 220 and the second dielectric cell 240. As further described herein, the first dielectric cell 220 supplies supply gas containing ozone gas to the second dielectric cell 240. The second dielectric cell 240 creates additional ozone gas in the supply gas and supplies the ozone gas to the injector 252, and the injector 252 mixes the ozone gas into the water in order to form the ozonated liquid that is discharged from the unit 10 at the liquid output port 132.

The injector 252 forms the ozonated liquid by mixing ozonated gas with the water. Suitable injectors are commercially available from the Mazzei Injector Corporation. The injector 252 uses a pressure differential between the water entering the injector 252 from the liquid line 218 and the fluid exiting the injector 252 to mix the water with ozone gas. The pressure at an inlet port of the injector 252 is higher than the pressure at an outlet port of the injector 252, and this pressure differential creates a suction in the injector 252 that draws the ozone gas from the second dielectric cell 240 into the injector 252 for mixing with the water.

An important feature of the unit 10 is the use of multiple dielectric cells, namely, the first dielectric cell 220 and the second dielectric cell 240. The first dielectric cell 220 prepares ozone gas that is supplied to the second dielectric cell 240, which creates additional ozone gas, thus creating a highly concentrated supply of ozone gas that is supplied to the injector 250. In other embodiments, additional dielectric cells may be employed.

With reference to FIG. 5, top-down view of the unit 10 is shown. Ambient air is drawn into the first dielectric cell 220 via an ambient air input 224 of a first gas input trap 223. The first gas input trap 223 is sealingly connected to and surrounds a first end 221 of the first dielectric cell 220. The first dielectric cell 220 makes ozone gas from the ambient air passing through the first dielectric cell 220.

The first dielectric cell 220 includes a glass or other insulating cylinder. An electrical conductor passes through the cylinder. A conductive metal lattice, metal mesh, or coil wire surrounds the conductor. When power is supplied to the first dielectric cell 220, electricity passes through the conductor and sparks and arcs. This electrical discharge splits the oxygen molecules creating ozone gas from the oxygen molecules present in the ambient air inside of the dielectric cell 220. This method is generally referred to as corona discharge. The second dielectric cell 240 is constructed similar to the first dielectric cell 220.

As described above, ozone gas created by the coronal discharge in the first dielectric cell 220 is captured and supplied to the second dielectric cell 240. The supply gas from the first dielectric cell 220 to the second dielectric cell 240 contains an amount of ozone gas. A second or output end 222 of the first dielectric cell 220 is sealingly connected to and surrounded by a first gas output trap 227. The first gas output trap 227 funnels the ozone gas created by the first dielectric cell 220 to a first gas line 230 which is in fluidic communication with a second gas input trap 243 and an ozone gas input 244 on the second gas input trap 243. The first gas line 230 thus connects to the first gas output trap 227 to the ozone gas input 244. The second gas input trap 243 is sealingly connected to a first or input end 241 of the second dielectric cell 240. As such, supply gas to the second dielectric cell 240 already includes a first amount of ozone gas. The supply gas from the first dielectric cell 220 is further processed by the second dielectric cell 240 to add an additional amount of ozone gas to the supply gas.

The first gas output trap 227 seals the output of ozone gas from the first dielectric cell 220 such that nearly all of the ozone gas created by the first dielectric cell 220 or the output of gas from the first dielectric cell 220 is supplied in a closed communication via the first gas line 320 to the second dielectric cell 240. The closed communication provides for the second dielectric cell 240 to form ozone gas from the output gas of the first dielectric cell 220.

The ozonated gas produced by the second dielectric cell 240 is transported via a second gas line 260 to an injector gas input port 254 of the injector 252. The second gas output trap 247 is sealingly connected to a second or output end 242 of the second dielectric cell 240.

The use of the first and second dielectric cell 220 and 240 creates an increased concentration of ozone gas in supply communication with the injector 252. A single dielectric cell similar to the first dielectric cell 220 or the second dielectric cell 240 creates ozone gas at a concentration of 0.5 parts per million. However, the use of two of the two inline dielectric cells, i.e., the first dielectric cell 220 and the second dielectric cell 240, creates a supply of ozone gas to the injector 252 having a concentration of approximately 1.3 ppm of ozone.

The unit 10 is electrically connected to the power supply 138, such as a 115-volt power supply. The electrical connector 136 of the unit 10 is in electrical communication with a first power supply 320 and a second power supply 340. A first electrical supply line 322 is in electrical communication with the first power supply 320 and at a conductor positioned at the first end 221 of the first dielectric cell 220. A second electrical supply line 342 is in electrical communication with the second power supply 340 and at a conductor positioned at the first end 241 of the second dielectric cell 240. The electrical supply lines 322 and 342 provide the electricity for the corona discharge.

Turning now to FIG. 7, the ozone faucet 233 has been replaced with a spray nozzle 400 having a handle 410 to actuate the discharge of the ozonated liquid. The spray nozzle 400 is in fluidic communication with the liquid output port 132. A hose, tube or other liquid communication structure 405 is used to supply the sprayer 400 with the ozonated liquid from the liquid output port 132. The spray nozzle 400 or the liquid communication structure 405 includes a valve means or other shut-off to control the output of liquid from the spray nozzle. For example, a handle 410 of the spray nozzle 400 may actuate the valve or otherwise control the flow of the ozonated liquid from the spray nozzle 400. The spray nozzle 400 may be used to spray fruits and vegetables in order to kill microorganisms, remove dirt and debris, and/or wash of pesticide residue.

The spray nozzle 400 may further be used to clean and sanitize shower areas and rest rooms. Spraying the ozonated liquid onto such bathroom surfaces is an economical and convenient method to provide for sanitation. The ozonated liquid does not leave a residue or film on the restroom and shower surfaces. No other chemicals or detergents are required. There is no clean-up or storage of soiled conventional cleaning tools, such as a mop or mop bucket.

The unit 10 provides a flow of ozonated liquid at approximately 25 psi and 1.5 gallons per minute from the ozone faucet 233 or the spray nozzle 400. The ozonated liquid has an ozone concentration of approximately 1.8 parts per million.

The unit 10 also finds utility in cleaning fruits and vegetables. Herbicide residue may be removed from the fruit and vegetable surfaces. Pathogens, such as salmonella, may be easily removed from more delicate food surfaces, such as that of a tomato. Raw meats and carcasses and may also be directly contacted with the ozonated liquid.

The unit 10 may also be used to clean and sterilize medical instruments. The unit 10 may also be used for general hand-washing and wound-flushing. The unit 10 may also be used for drain cleaning. The oxidation provided by the ozonated liquids will break-up many deposits in drains.

In operation of the unit 10, the user actuates the handle 235 of the ozone faucet 233. When the cold water begins to flow through the liquid input line 200 to the unit 10, the liquid flow switch 215 activates the first power supply 320 and the second power supply 340 to discharge electrical current to the first dielectric cell 220 and the second dielectric cell 240 to the begin creation of ozone gas. Generally, the operator should expect to wait several seconds for the water flowing from the ozone faucet 233 to transition to ozonated liquid. When the handle 235 is turned off, water flow through the unit 10 is stopped and the liquid flow switch 215 turns the first power supply 320 and the second power supply 340 off.

A reaction vessel 500 is shown in FIGS. 9-13. The reaction vessel 500 may be used to process ozonated fluid to reduce the bubble size of the ozone gas in the ozonated fluid. The reaction vessel 500 may be connected to the output of an ozonated liquid dispensing unit. The reaction vessel 500 receives the ozonated fluid, processes the ozonated fluid, and outputs the processed ozonated fluid. Faucets, sprayers, applicators, and other dispensing systems may receive the ozonated fluid from the reaction vessel 500. For example, the reaction vessel 500 may be used with the ozonated liquid dispensing unit 10 shown in FIGS. 1-8. For example, the reaction vessel 500 may be used with the ozonated liquid dispensing unit 10 shown in FIG. 3 and plumbed into the faucet/sink combination 345.

Figure 14:
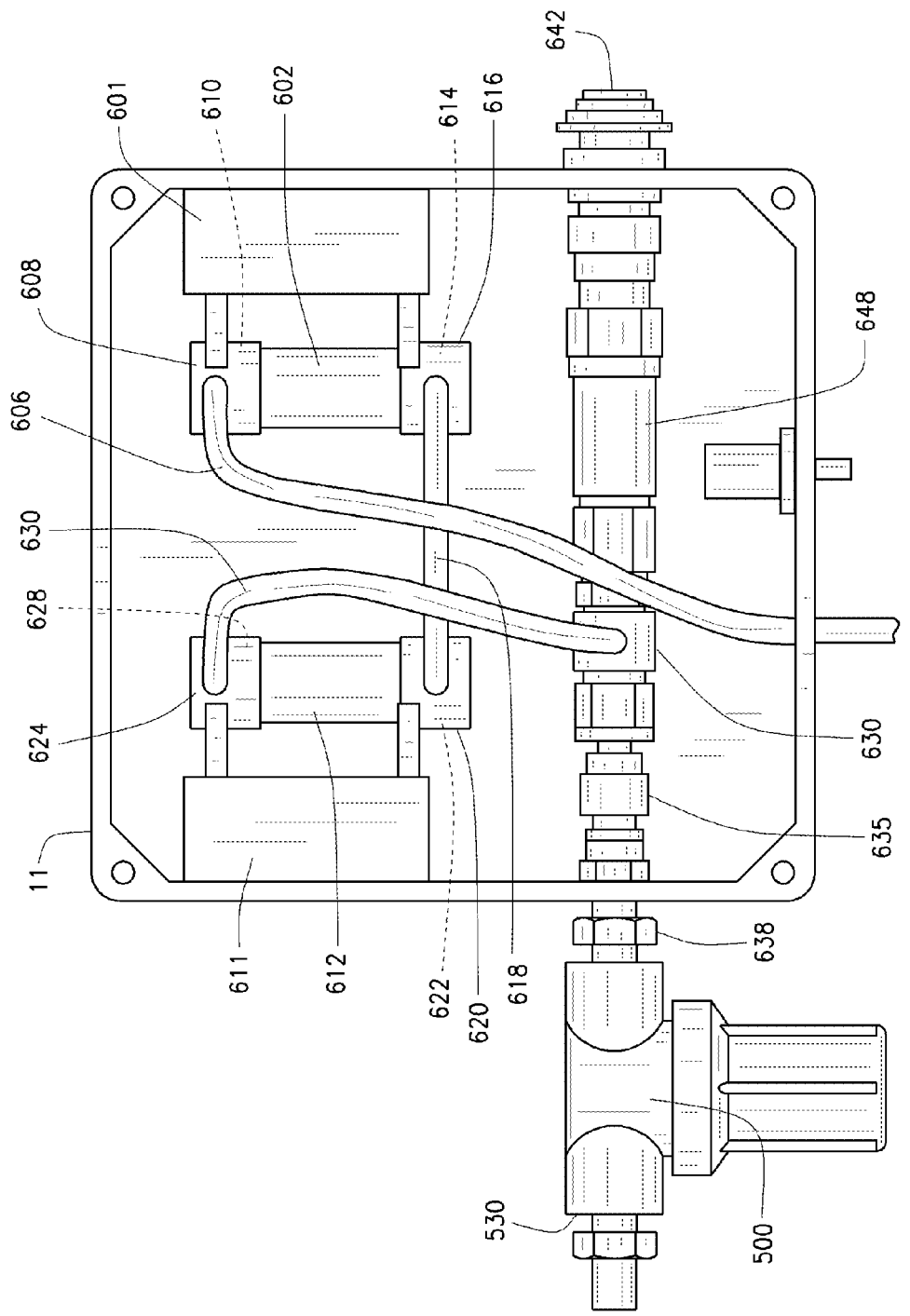
FIG. 14 is a top-down view of the ozonated liquid dispensing unit with the reaction vessel attached.

A further embodiment of the ozonated liquid dispensing unit is shown in FIG. 14. An ozonated liquid dispensing unit 11 is shown with the reaction vessel 500 in FIG. 14. The ozonated liquid dispensing unit 11 generally operates in a similar manner to the ozonated liquid dispensing unit 10, which is shown in FIGS. 1-8. The ozonated liquid dispensing unit 11 is described below in greater detail.

As shown in FIG. 14, the reaction vessel 500 is in fluidic communication with a liquid output port 638 of the ozonated liquid dispensing unit 11. The liquid output port 638 discharges the ozonated fluid prepared by the ozonated liquid dispensing unit 11 into the reaction vessel 500 for processing.

The reaction vessel 500 further processes the ozonated fluid to reduce the bubble size of the ozone gas in the ozonated fluid. The reaction vessel 500 further reduces the number of ozone gas bubbles in the ozonated fluid to increase the concentration of ozone in the ozonated fluid. Decreasing the bubble size of the ozone gas also assists in maintaining a uniform concentration of ozone gas in the ozonated fluid. The processing by the reaction vessel 500 and its components are further described below.

Figure 13:
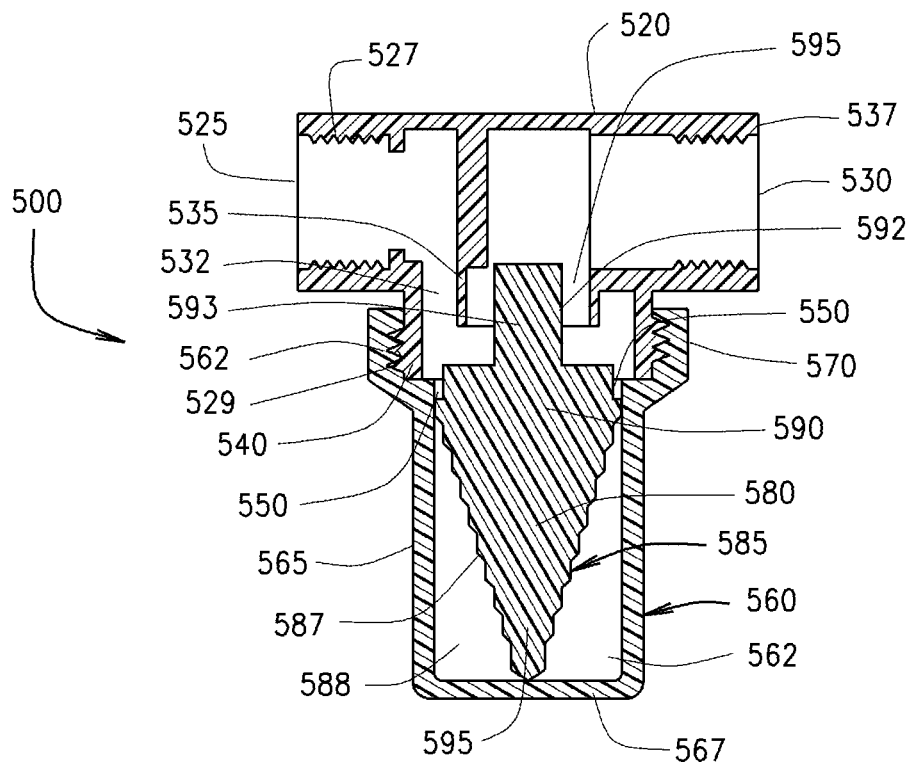
FIG. 13 is a cross-sectional view of the reaction vessel.

As shown in FIG. 13, the reaction vessel 500 includes an assembly 520 that receives a container 560, which defines an open volume 562. The container 560 forms a cup-like structure to hold the core 580. The container 560 has container walls 565 that help to position the core 580. The container 560 contains the core 580 in the open volume 562. The container 560 defines a container rim 570 that engages the assembly 520.

Generally, the ozonated fluid from the liquid output port 132 of the unit 10 or the liquid output port 638 of the unit 11 enters a fluid entry opening 525 of the assembly 520 and the ozonated fluid passes into the container 560, where it is processed about the core 580. Then, the processed ozonated fluid exits the assembly 520 via the fluid exit opening 530 and to the sprayer 400, other sprayers, other systems, or other distributors and/or applicators.

Figure 10:
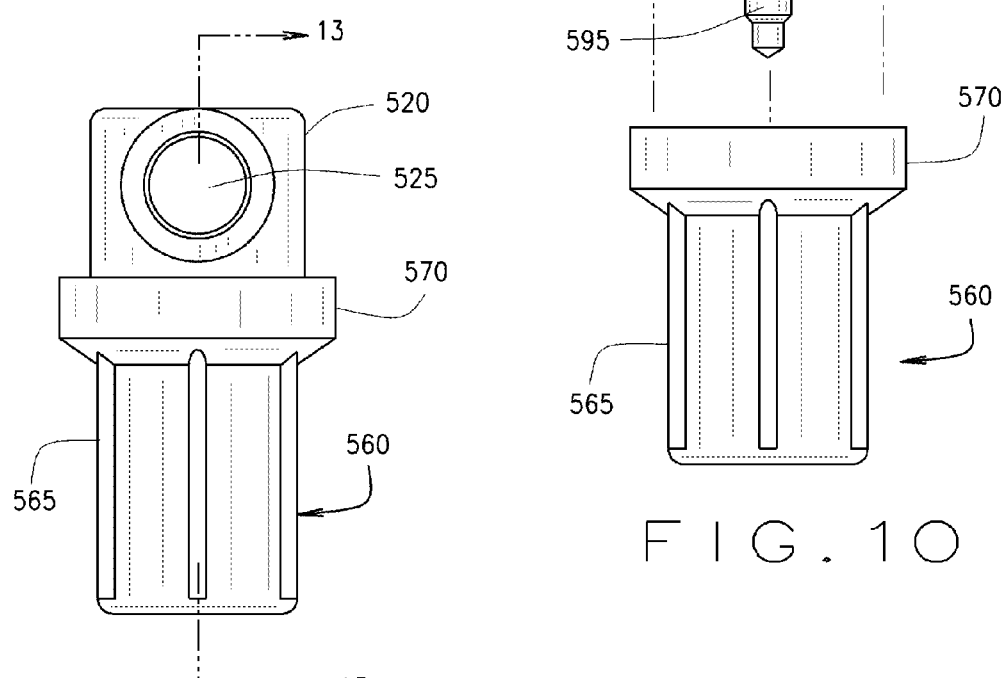
FIG. 10 is an exploded view of the reaction vessel.
Figure 11:
FIG. 11 is an end view of the reaction vessel.
Figure 12:
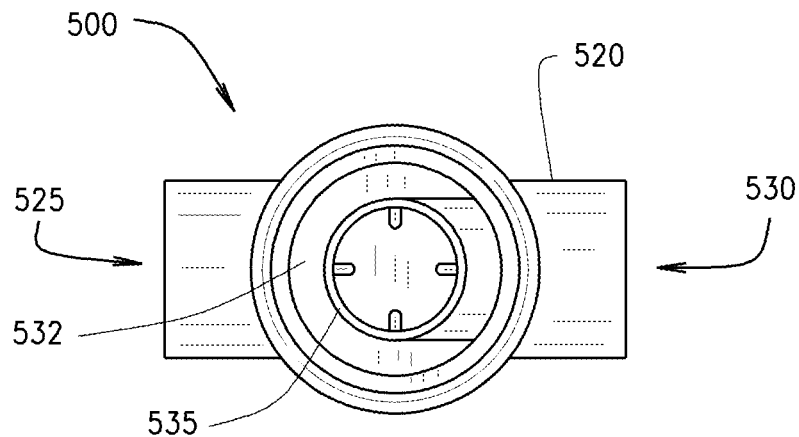
FIG. 12 is a bottom view of the reaction vessel.

The assembly 520 receives the container 560 in a threadable engagement. As shown in FIG. 10, a lower assembly wall 540 of the assembly 520 includes assembly threads 529. The assembly threads 529 are in a threadable engagement with container threads 562 of the container rim 570. The container 560 is threadably attached or connected to the assembly 520 via the engagement of the container threads 562 and the assembly threads 529.

The container 560 includes container walls 565 that surround the core 580. An annulus 588 in the open volume 562 is provided between the container walls 565 and the core 580. The annulus 585 provides a space for the ozonated fluid to circulate about the core 580.

The core 580 includes a solid, cone-shaped structure. The ozonated fluid circulates about a ridged surface 585 of the core 580. The core 580 includes a wider portion 590 closer to the container rim 570, and the core 580 includes a narrower portion 595 near a bottom 567 of the container 570. The wider portion 590 is close to or just less than in size compared to an internal diameter of the container 560. An annular gap 550 is located between the wider portion 590 and the container wall 565. The fluid entry opening 525 is in fluidic communication with the annulus 588 via the annular gap 550. The fluid exit opening 530 is in fluidic communication with the annulus 588 via the annular gap 550.

An outer surface of the core 580 includes the ridged surface 585. The ridged surface 585 includes a plurality of ridges 587 that assist in crushing and breaking the bubbles of ozone gas in the ozonated fluid as the ozonated fluid circulates and swirls about the ridged surface 585. In the embodiment shown in FIG. 10, the ridged surface 585 includes approximately 9 to approximately 12 ridges 587. Other embodiments may include approximately 5 to approximately 30 ridges 587. The number of ridges 587 provided on the ridged surface 585 will vary depending upon the size of the core 580 and the reaction vessel 500, the amount of fluid to be processed in the reaction vessel 500, as well as other variables. The core 580 further includes a stem 593 extending from the wider portion 590. The core 580 extends into a fluid exit outlet 535 of the assembly 520.

The ozonated fluid from the ozonated liquid dispensing unit 11 enters the reaction vessel 500 at the fluid entry opening 525. The fluid entry opening 525 may include threads 527 to threadably engage to a liquid output port 638 of the ozonated liquid dispensing unit 11. In other embodiments, a hose or fluid line may connect the ozonated liquid dispensing unit 11 and the reaction vessel 500.

The ozonated fluid passes through a fluid entry passage 532 of the reaction vessel 500 that is defined by the lower assembly wall 540 and the fluid exit outlet 535. The lower assembly wall 540 extends downward between the fluid entry opening 525 and the fluid exit opening 530. The ozonated fluid next passes through the annular gap 550 between the ridged surface 585 of the wider portion 590 of the core 580 and the container wall 565. The ozonated fluid next circulates and flows about the interior of the container 560 in the annulus 588.

The ozonated fluid is under pressure from the flow of fluid through the ozonated liquid dispensing unit 11. This pressure urges the ozonated fluid to contact the ridged surface 585, which crushes and reduces the size of ozone gas bubbles in the ozonated fluid. The ozonated fluid next exits the container 560 through the annular gap 550 and enters an annular fluid exit passage 595 of the fluid exit outlet 535. The fluid exit outlet 535 is in fluidic communication with the fluid exit opening 530. The ozonated fluid then passes through the fluid exit opening 530 and onto the fluid supply line 405, sprayer, hoses, lines, or distribution assembly. The fluid exit opening 530 may include threads 537 to engage to such spraying and/or distribution structures.

The fluid exit outlet 535 defines the annular fluid exit passage 595, which is the opening between the walls forming the fluid exit outlet 535 and an outer circumference 592 of the stem 593 of the core 580. The stem 593 is loosely positioned in the fluid exit outlet 535. The loose engagement of the stem 593 into the fluid exit outlet 535 assist in maintaining an upright position for the core 580.

The assembly 520, the core 580 and the container 560 may be constructed from a variety of materials, such as plastics, metals or metal alloys. The assembly 520, the container 560 and the core 580 are well suited for manufacturing by injection molding. The container 560 may further clamp or snap fit onto the assembly 520.

The ozonated liquid dispensing units 10 and 11 may be incorporated into a variety of systems, applicators, platforms, etc. that are suitable for use in a variety of applications, industries, and manners that use, spray, apply or otherwise utilize an ozonated fluid in order to clean, sanitize, disinfect, etc. For example, the ozonated liquid dispensing units 10 and 11 may be incorporated into portable kitchen systems, mobile hospital cleaning equipment, floor/carpet cleaners, air scrubbers, etc.

The ozonated liquid dispensing unit 11 will now be described with reference to FIG. 14. The ozonated liquid dispensing unit 11 functions similarly to the ozonated liquid dispensing unit 10, i.e., feed gas is passed through two ozone generators arranged in a serial manner with the output gas from a first ozone generator supplying the second ozone generator. The ozonated liquid dispensing unit 11 may be used with or without the reaction vessel 500 shown in FIGS. 9-13. Of course, the use of the reaction vessel 500 will provide an ozonated solution with improved cleaning and sanitizing characteristics.

Oxygen gas is produced by an oxygen concentrator or generator 600. The oxygen gas is drawn into a first dielectric cell 602 via a first gas line 606. A first oxygen gas input trap 608 is sealingly connected to and surrounds a first end 610 of the first dielectric cell 602. The first gas line 606 connects the oxygen has input trap 608 and the oxygen concentrator 600. The first dielectric cell 602 makes ozone gas from the oxygen gas passing through the first dielectric cell 602.

Similar to the other embodiments described herein, the first dielectric cell 602 includes a glass or other insulating cylinder. An electrical conductor passes through the cylinder. A conductive metal lattice, metal mesh, or coil wire surrounds the conductor. When power is supplied to the first dielectric cell 602, electricity passes through the conductor and sparks and arcs. This electrical discharge splits the oxygen molecules creating ozone gas from the oxygen molecules present in the ambient air inside of the first dielectric cell 602. This method is generally referred to as corona discharge. A second dielectric cell 612 is constructed similar to the first dielectric cell 602. Power cells 601 and 611 supply the first and second dielectric cells 602 and 612 with the power.

As described above, ozone gas created by the coronal discharge in the first dielectric cell 602 is captured and supplied to the second dielectric cell 612. The supply gas from the first dielectric cell 602 to the second dielectric cell 612 contains an amount of ozone gas. A second or output end 614 of the first dielectric cell 602 is sealingly connected to and surrounded by a first gas output trap 616. The first gas output trap 616 funnels the ozone gas created by the first dielectric cell 602 to a second gas line 618 which is in fluidic communication with a second gas input trap 620. The second gas line 618 thus connects to the first gas output trap 616 and to the second gas input trap 620. The second gas input trap 620 is sealingly connected to a first or input end 622 of the second dielectric cell 240. As such, supply gas to the second dielectric cell 612 already includes a first amount of ozone gas. The supply gas from the first dielectric cell 602 is further processed by the second dielectric cell 612 to add an additional amount of ozone gas to the supply gas.

The first gas output trap 616 seals the output of ozone gas from the first dielectric cell 602 such that nearly all of the ozone gas created by the first dielectric cell 602 or the output of gas from the first dielectric cell 602 is supplied in a closed communication via the second gas line 618 to the second dielectric cell 612. The closed communication provides for the second dielectric cell 612 to form ozone gas from the output gas of the first dielectric cell 602.

The second gas output trap 624 is sealingly connected to a second or output end 628 of the second dielectric cell 612. The ozonated gas produced by the second dielectric cell 612 is transported via a third gas line 630 to the injector 630.

The ozonated liquid dispensing unit 11 further includes the injector 630. The injector 630 may be a chemical injector commercially available from Dultmeier Sales in Omaha, Nebr., under the trade name, Chem Flex Injectors as part number HF 110057. The injector 630 uses a check-ball to prevent backflow into the injector 630.

Water enters a liquid input port 642. The water is directed through a fluid flow switch 648, which activates the first dielectric cell 602 and the second dielectric cell 612. A suitable flow switch for the fluid flow switch 648 includes a Series 5 Erecta Switch from OKI Sensor Device Corporation. Next, the water passes to the injector 630, which injects the water with the ozone gas. The injector 630 accommodates flow rates through the ozonated liquid dispensing unit 11. The supply of fresh water to the ozonated liquid dispensing unit 11 may vary depending on other uses in the water supply system, seasonal changes in water pressure, as well as other peak and off peak usage levels of the fresh water. From the injector 630, the ozonated fluid passes to fluidic connectors 635 which pass the ozonated fluid to the reaction vessel 500 via a liquid output port 638.

The ozonated liquid dispensing unit 11 provides a flow rate of approximately ½ gallon per minute to approximately 15 gallons per minute at a concentration of approximately 0.05 ppm to approximately 5 ppm. The ozonated liquid dispensing unit 11 may be scaled up or down to increase or decrease the amount of flow of ozonated fluid. The ozonated liquid dispensing unit 11 may be integrated or incorporated into a variety of systems or platforms that spray or apply an ozonated fluid.

Another embodiment of a reaction vessel for an aqueous ozone solution is also described. The reaction vessel is used to break up the bubbles of ozone gas that have been injected into water forming the aqueous ozone solution. The reaction vessel breaks up the bubbles of ozone gas into nanobubbles of ozone gas. The reaction vessel also further mixes the ozone gas into the water.

The reaction vessel generally includes a housing that contains a contact member that assists in breaking up the bubbles of the ozone gas into uniform size. The contact member is positioned in the interior of the housing, and the incoming aqueous ozone solution is directed against the contact member.

Typically, an injector receives a supply of ozone gas from an ozone gas generation unit or system. Typically, the injector also receives a supply of water or other liquid, and the injector injects the ozone gas into the water to form the aqueous ozone solution. The reaction vessel further mixes the ozone gas into the aqueous ozone solution. The reaction vessel breaks up the bubbles of ozone gas to have a more uniform size distribution and to reduce the bubbles to nanobubbles. The uniform size distribution of the ozone gas bubbles helps to maintain the ozone gas in solution for longer periods of time. Since the bubbles of ozone gas have a narrow size range distribution, the bubbles tend to remain in solution instead of breaking up or off-gassing. By having bubbles of a more consistent size distribution, the bubbles tend to have less movement in the aqueous ozone solution, which provides for the solution to maintain its oxidation reduction potential for extended periods of time.

The reaction vessel passes the ozonated solution against and past a contact member that helps break up the bubbles. In one aspect, the contact member includes a cone. The ozone solution is directed toward a first, narrow end of the cone. The ozone solution contacts and circulates past and around the cone. The cone is maintained in a housing, which receives the ozonated solution and contains the ozonated solution during the processing. The housing includes an entry port and an exit port. The entry port is in fluidic communication with the injector via hoses, tubing, conduits, passages, pipes, etc. to receive the ozonated fluid. The exit port is in fluidic communication with hoses, tubing, conduits, passages, pipes, etc. of a distribution system, apparatus, sprayer, or other device that uses or employs the ozonated fluid.

The contact member may include a plurality of ridges, steps, or other surfaces that physically break up the bubbles of ozone gas passing against and by the contact surface. The plurality of ridges, steps, or other surfaces may cause turbulence in the flow of the ozonated solution to further break up the bubbles.

Figure 20:
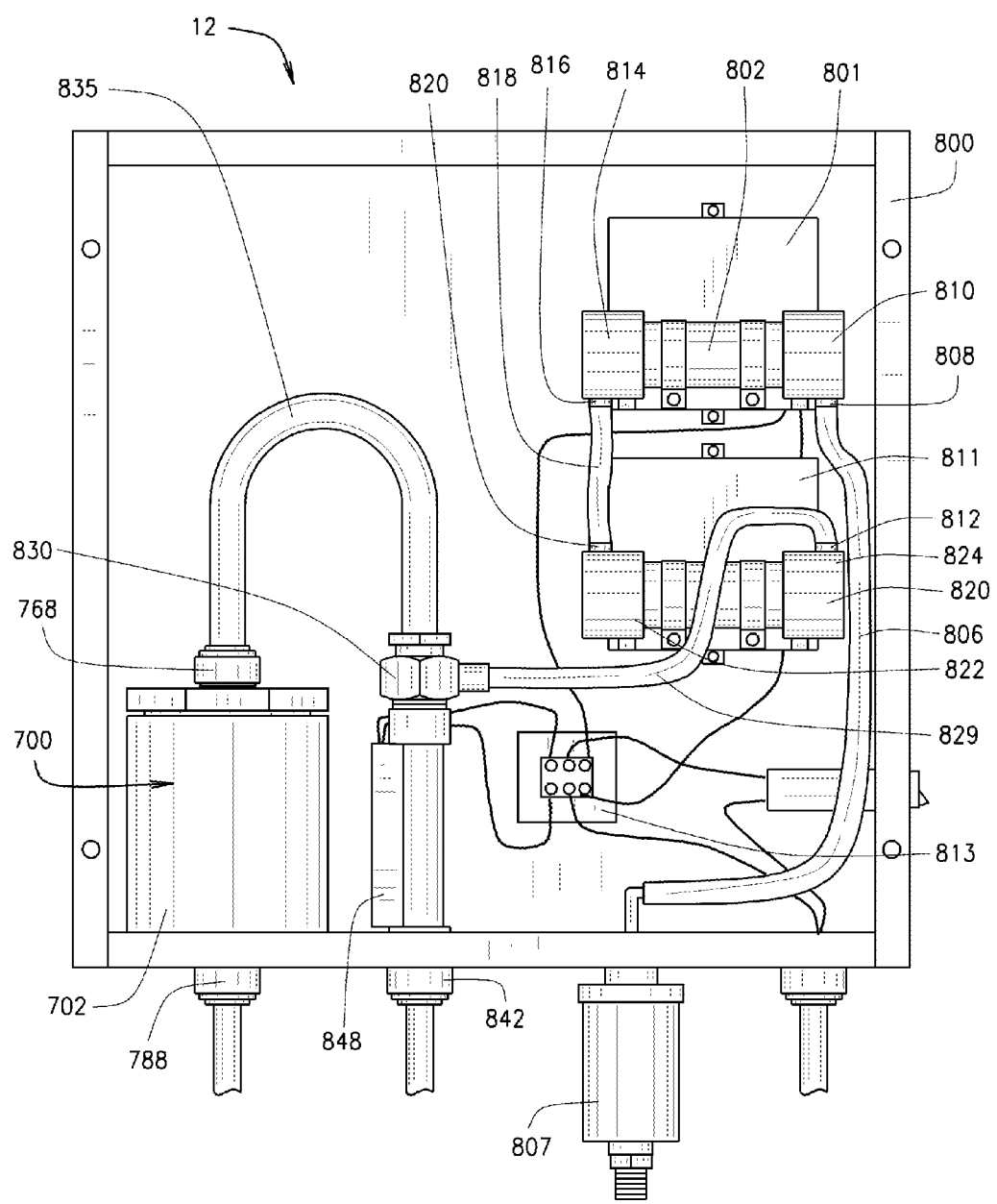
FIG. 20 is a top-down view of the ozonated liquid dispensing unit incorporating the reaction vessel.

The reaction vessel will now be described with reference to FIGS. 15-19, in which a reaction vessel 700 is shown. A further embodiment of the ozonated liquid dispensing unit is shown in FIG. 20, in which an ozonated liquid dispensing unit 12 incorporates the reaction vessel 700. The ozonated liquid dispensing unit 12 generally operates in a similar manner to the ozonated liquid dispensing units 10 and 11, which are shown in FIGS. 1-14. The ozonated liquid dispensing unit 12 is described below in greater detail. Although the reaction vessel 700 is shown incorporated into the ozonated liquid dispensing unit 12, the reaction vessel 700 may be used with other types and styles of ozonated liquid dispensing units and systems.

The reaction vessel 700 generally includes a housing 702, a cone 720, a first end 750, and a second end 770. The ozonated solution enters the housing 702 via the first end 750. The housing 702 has a generally hollow interior 704. The cone 720 is positioned in the interior 704 of the housing 702. The ozonated solution flows past and against the cone 720 and exits the housing 702 via the second end 770.

During assembly of the reaction vessel 700, the first end 750 is inserted into a first housing opening 705 of the housing 702, while a second end 770 is inserted into a second housing opening 707 of the housing 702. The cone 720 is positioned in the interior 704 of the housing 702 and is loosely held in position by the first end 750 and the second end 770.

The housing 702 has an inner surface 706 that is generally smooth except for an annular ridge 708, which extends into the interior 704 of the housing 702. As shown in an exploded view of the reaction vessel 700 in FIG. 17, an insert portion 760 of the first end 750 is inserted into the first housing opening 705 of the housing 702 until the insert portion 760 approximately abuts the annular ridge 708. Likewise, an insert portion 780 of the second end 770 is inserted into the second housing opening 707 until the insert portion 780 approximately abuts an opposite surface of the annular ridge 708. As such, the insert portions 760 and 780 fit into opposite ends of the housing 702, and the cone 720 is positioned between the opposite ends.

The housing 702 has a generally cylindrical shape having a length 710 that is generally greater than a width 712. The housing 702 has an inner diameter 714 that is greater than an outer diameter 736 of the cone 720. The first end 750 generally includes a rim portion 756 and the insert portion 760. Likewise, the second end 770 generally includes a rim portion 776 and the insert portion 780.

The insert portions 760 and 780 of the first end 750 and the second end 770 include walls 762 and 782, respectively, which are positioned flush against the interior surface 706 of the housing 702. A frictional engagement may hold the walls 762 and 782 against the interior surfaces 706 of the housing 702. Glue, adhesives, epoxy, sealants, etc. may also be used to seal the housing 702 with the walls 762 and 782.

The first end 750 also includes a central opening 752 that allows the ozonated fluid to enter the housing 702. The second end 770, likewise, has a central opening 772 that allows the ozonated fluid to exit from the housing 702. A first coupling 768 and a second coupling 788 may fit into the central openings 752 and 772, respectively, in order to plumb or fluidly connect the reaction vessel 700 with the remainder of the system or apparatus that is producing the ozonated fluid.

Figures 15, 16:
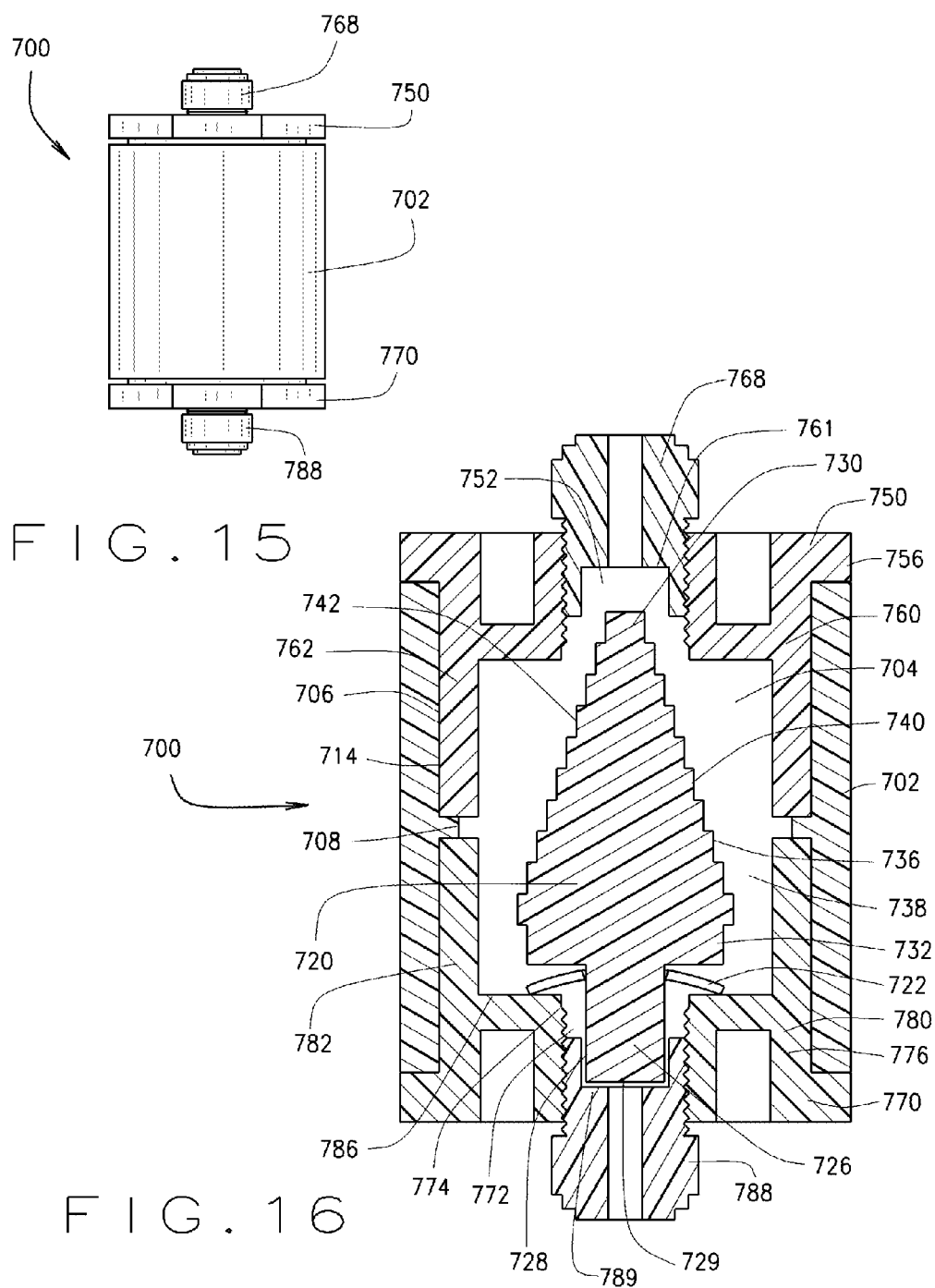
FIG. 15 is a front view of the reaction vessel.
FIG. 16 is a sectional view of the reaction vessel.

The cone 720 will now be described with reference to FIG. 16. The cone 720 includes a first end 730 opposite of a second end 732. The cone 720 includes a solid, cone-shaped body. The cone 720 is positioned between the central openings 752 and 772. The first end 730 generally has a smaller external diameter than an external diameter of the second end 732. The cone 720 further includes a stem 726. The stem 726 extends from the second end 732 of the cone 720. The stem 726 may extend from a generally center portion of a rear surface of the second end 732. The stem 726 may extend from the second end 732 along a vertical axis of the cone 720. The stem 726 may be integral with the second end 732 of the cone 720. An exterior of the cone 720 includes a contact surface 740. The contact surface 740 may extend between the first end 730 and the second end 732. The contact surface 740 may include a plurality of ridges or steps 742 that contact the ozonated fluid. The plurality of ridges or steps 742 may progressively increase in diameter from the first end 730 to the second end 732. The plurality of ridges or steps 742 of the contact surface 740 assist in breaking up the bubbles of ozone gas in the ozonated fluid and further mixing the ozone gas with the water. The contact surface 740 may include 3 to 30 or more ridges or steps 742. The number of ridges or steps 742 may depend on the size of the cone 720 and particular application in which the cone 720 is used. The contact surface 740 assists in breaking up the bubbles of ozone gas in the ozonated fluid into ozone nanobubbles, which are bubbles of gas having a diameter of approximately several hundred nanometers or below. Essentially all of the ozone gas in the ozonated fluid is contained in nanobubbles of ozone gas. The ozonated fluid may be used to create a film, layer or blanket of nanobubbles that may last for several hours to several days on a work or other surface. The nanobubbles of ozone gas creates a uniform, dense and longer lasting coating of an aqueous ozone solution. The use of nanobubbles provides an antibacterial layer on the surface, which reduces the risk of surface contamination or bio-fouling.

The cone 720 generally increases in external diameter from the first end 730 to the second end 732. During use of the reaction vessel 700, the ozonated fluid is directed into the reaction vessel 700 such that the first end 730 of the cone 720 is positioned in the incoming flow of the ozonated fluid. As such, the ozonated fluid is first directed against the smaller first end 730 of the cone 720. The ozonated fluid flows against the contact surface 740 of the cone 720. The ozonated fluid circulates about the contact surface 740 to break up the bubbles of ozone gas against the contact surface 740. The ozonated fluid passes the cone 720 in an annular fluid passage 738 that is formed between the contact surface 740 of the cone 720 and the combination of the inner surface 706 of the housing 702 and the walls 762 and 782 of the first insert portion 760 and the second insert portion 780, respectively.

The stem 726 of the cone 720 loosely fits into the central opening 772 of the second end 770. A spacer 722 is fitted over the stem 726. The spacer 722 has a spacer opening 724 that receives the stem 726. The spacer opening 724 is slightly larger than an outer diameter 728 of the stem 726. The spacer 722 has a generally curved or angled shape to position the second end 732 of the cone 720 spaced away from the central opening 772 such that the second end 732 of the cone 720 does not block or fully occlude the central opening 772, which allows the ozonated fluid to pass through the central opening 772. The spacer 722 may rest against an end surface 786 of the insert portion 780. The outer diameter 728 of the stem 726 is smaller than a central opening wall 774 of the central opening 772 to provide a fluid passage between the outer diameter 728 of the stem 726 and the central opening wall 774.

The cone 720 has an overall length that provides for the first end 730 of the cone 720 to enter the central opening 752 while the stem 726 enters the central opening 772. This arrangement loosely holds the stem 726 in its intended position, i.e., the cone 720 is held generally centrally in the housing 702 and general vertically aligned with respect to the length 710 of the housing 702. The cone 720 generally has a solid shape. The cone 720 may be molded from a variety of conventional thermoplastics.

The first coupling 768 and the second coupling 788 may be inserted or threadably attached to the central openings 752 and 772, respectively. Each of the first coupling 768 and the second coupling 788 may include a recessed portion 769 and 789, respectively that receives the tip 731 of the first end 730 or a base surface 729 of the stem 726. The first coupling 768 may fluidly connect to hoses, tubing, conduits, passages, pipes, etc. that supply the reaction vessel 700 with the ozonated fluid. The second coupling 788 may fluidly connect to hoses, tubing, conduits, passages, pipes, etc. to output the processed ozonated fluid from the reaction vessel 700. Each of the first coupling 768 and the second coupling 788 include a fluid passage or opening.

The ozonated liquid dispensing unit 12, shown in FIG. 20 incorporates the reaction vessel 700. The reaction vessel 700 may be included within or inside of a housing 800 of the ozonated liquid dispensing unit 12.

The ozonated liquid dispensing unit 12 may draw air from its environment or be supplied with oxygen gas from an oxygen concentrator or generator. The air or oxygen gas provides supply gas to a first dielectric cell 802 via a first gas line 806. A first supply gas input trap 808 is sealingly connected to and surrounds a first end 810 of the first dielectric cell 802. The first gas line 806 connects to the supply gas input trap 808. The first dielectric cell 802 makes ozone gas from the supply gas passing through the first dielectric cell 802. An air filter dryer 807 may first filter and dry the air before passing the air to the first gas line 806. A suitable dryer 807 is commercially available from SPEED-AIR as model 6ZC63.

Similar to the other embodiments described herein, the first dielectric cell 802 includes a glass or other insulating cylinder. An electrical conductor passes through the cylinder. A conductive metal lattice, metal mesh, or coil wire surrounds the conductor. When power is supplied to the first dielectric cell 802, electricity passes through the conductor and sparks and arcs. This electrical discharge splits the oxygen molecules creating ozone gas from oxygen molecules present in the supply gas inside of the first dielectric cell 802. This method is generally referred to as corona discharge. A second dielectric cell 812 is constructed similar to the first dielectric cell 802. The first and second dielectric cells 802 and 812 are commercially available from Alta Industries as models PA-021. Each of the first and second dielectric cells 802 and 812 may provide 250 mg of ozone gas per hour. Power cells 801 and 811 supply the first and second dielectric cells 802 and 812 with the power. A relay 813 electrically connects the power cells 801 and 812 with a fluid flow switch 848. The relay 813 may include a button pack relay commercially available from Compaq Engineering Inc.

As described above, ozone gas created by the coronal discharge in the first dielectric cell 802 is captured and supplied to the second dielectric cell 812. The supply gas from the first dielectric cell 802 to the second dielectric cell 812 contains an amount of ozone gas. A second or output end 814 of the first dielectric cell 802 is sealingly connected to and surrounded by a first gas output trap 816. The first gas output trap 816 funnels the ozone gas created by the first dielectric cell 802 to a second gas line 818 which is in fluidic communication with a second gas input trap 820. The second gas line 818 thus connects to the first gas output trap 816 and to the second gas input trap 820. The second gas input trap 820 is sealingly connected to a first or input end 822 of the second dielectric cell 812. As such, supply gas to the second dielectric cell 812 already includes a first amount of ozone gas. The supply gas from the first dielectric cell 802 is further processed by the second dielectric cell 812 to add an additional amount of ozone gas to the supply gas.

The first gas output trap 816 seals the output of ozone gas from the first dielectric cell 802 such that nearly all of the ozone gas created by the first dielectric cell 802 or the output of gas from the first dielectric cell 802 is supplied in a closed communication via the second gas line 818 to the second dielectric cell 812. The closed communication provides for the second dielectric cell 812 to form ozone gas from the output gas of the first dielectric cell 802.

The second gas output trap 824 is sealingly connected to a second or output end 828 of the second dielectric cell 812. The ozonated gas produced by the second dielectric cell 812 is transported via a third gas line 829 to the injector 830.

The ozonated liquid dispensing unit 12 further includes the injector 830. The injector 830 may be a chemical injector commercially available from Hyrdra Flex, Inc. under the trade name, Chem Flex Injector, as part number HF 110057. The injector 830 uses a check-ball to prevent backflow into the injector 830.

Water enters a liquid input port 842. The water is directed through a fluid flow switch 848, which activates the first dielectric cell 802 and the second dielectric cell 812. The water may simultaneously activate the first dielectric cell 802 and the second dielectric cell 812. A suitable flow switch for the fluid flow switch 848 includes a straight body polypropylene flow switch, such as a Series 5 Erecta switch commercially available from OKI Sensor Device Corporation. Next, the water passes to the injector 830, which injects the water with the ozone gas. The injector 830 accommodates flow rates through the ozonated liquid dispensing unit 12. The fluid flow switch 848 is positioned in the water flow before the water reaches the injector 830. The supply of fresh water to the ozonated liquid dispensing unit 12 may vary depending on other uses in the water supply system, seasonal changes in water pressure, as well as other peak and off peak usage levels of the fresh water. From the injector 830, the ozonated fluid passes through piping 835, which pass the ozonated fluid to the reaction vessel 700, via the first coupling 768, for additional mixing and processing. The further processed and mixed ozonated fluid exits the reaction vessel 700 through the second coupling 788.

The ozonated liquid dispensing unit 12 provides a flow rate of approximately ½ gallon per minute at a concentration of approximately 2.0 ppm to approximately 3.0 ppm. The ozonated liquid dispensing unit 12 may be scaled up or down to increase or decrease the amount of flow of ozonated fluid. The ozonated liquid dispensing unit 12 may be integrated or incorporated into a variety of systems or platforms that spray or apply an ozonated fluid in order to clean, sanitize, disinfect, etc.

Ozonated fluids produced by the ozonated liquid dispensing unit 12 were analyzed. During the production of the ozonated fluid, the reaction vessel 700 reduces a bubble size of ozone gas bubbles to create uniform-sized nanobubbles with a spherical geometry and thereby lowering the surface tension in the ozonated fluid. The nanobubbles may have a diameter of less than 300 nanometers. Cohesive forces among liquid molecules are responsible for the phenomenon of surface tension in the liquid. In the bulk of the liquid, each molecule of liquid is pulled equally in every direction by neighboring liquid molecules, resulting in a net force of zero. The molecules at the surface of the liquid do not have other molecules on all sides of them and therefore are pulled inwards. This creates some internal pressure and forces liquid surfaces to contract to the minimal area. As a result of this surface area minimization, a surface will assume the smoothest shape it can. Mathematical proof that "smooth" shapes minimize surface area relies on use of the Euler-Lagrange equation. Since any curvature in the surface shape results in greater area, a higher energy will also result, which in turn produces a higher oxidation-reduction potential for the ozonated fluid.

As the amount of oxidizer in the water is increased, the oxidizer "steals" electrons from the surface of a platinum measuring electrode, which is used to measure oxidation-reduction potential. When these negatively charged electrons are removed from this electrode, the electrode becomes more and more positively charged. As more oxidizer is added to the water, the electrode generates a higher and higher positive voltage. Consequently, the surface will push back against any curvature to minimize its gravitational potential energy. Surface tension is visible in other common phenomena, especially when surfactants are used to decrease it.

Ozone gas bubbles have very large surface areas with very little mass. Bubbles in pure water are unstable. Lowering the surface tension results in having a stabilizing effect on the bubbles, which is described by the Marangoni effect. This process makes the ozononated fluid acts like surfactant and actually reduces the surface tension by a factor of three or more. This process makes the ozonated fluid a type of emulsion and causes the solution to have a degreasing as well as a sanitizer effect on applied surfaces. Surface tension in the ozonated fluid water creates a sheet of ozonated fluid between the flow and the surface of the ozonated fluid. The surface of the ozonated fluid behaves like an elastic film increasing its surface area. The surface tension of water at 20 C is 72.8 mN/m. The surface tension results of the tested ozonated fluid, branded VIRIDITEC, was 49.1 mN/m or equal to the surface tension of hot water 60 C. The table below shows how the internal pressure of a water droplet increases with decreasing radius. For not very small drops the effect is subtle, but the pressure difference becomes enormous when the drop sizes approach the molecular size. (In the limit of a single molecule the concept becomes meaningless.)

| Droplet radius | 1 mm | 0.1 mm | 1 μm | 10 nm |
|---|---|---|---|---|
| Δp (atm) | 0.0014 | 0.0144 | 1.436 | 143.6 |

In the above tests, a Sigma Tensionmeter 701 was used to measure the surface tension. The Sigma tensionmeter 701 uses a Wilhelmy plate consisting of a thin plate usually on the order of a few square centimeters in area. The plate is often made from glass or platinum which may be roughened to ensure complete wetting. The plate is cleaned thoroughly and attached to a scale or balance via a thin metal wire. The force on the plate due to wetting is measured via a tensionmeter or microbalance and used to calculate the surface tension using the Wilhelmy equation:

$$\gamma = \frac{F}{l \cdot \cos\theta}$$

where l is the wetted perimeter (2w+2d) of the Wilhelmy plate and θ is the contact angle between the liquid phase and the plate. In practice the contact angle is rarely measured, instead either literature values are used, or complete wetting (θ=0) is assumed. When calculating surface tensions when using the Wilhelmy plate, a zero contact angle is assumed. In addition, because the plate is not moved during measurements, the Wilhelmy plate allows accurate determination of surface kinetics on a wide range of timescales and it displays low operator variance. In a typical plate experiment, the plate is lowered to the surface being analyzed until a meniscus is formed, and then raised so that the bottom edge of the plate lies on the plane of the undisturbed surface. If measuring a buried interface, the second (less dense) phase is then added on top of the undisturbed primary (denser) phase in such a way as to not disturb the meniscus. The force at equilibrium can then be used to determine the absolute surface or interfacial tension. Surface tension is therefore measured in forces per unit length. Its SI unit is newton per meter but the CGS unit of dyne per cm is also used. One dyn/cm corresponds to 0.001 N/m.

The ozonated fluids produced by the ozonated liquid dispensing unit 12 were also analyzed to measure zeta potential. The significance of zeta potential is that its value can be related to the stability of the ozonated solution. The zeta potential indicates the degree of repulsion between adjacent, similarly charged particles in a solution. For molecules and particles that are small enough, a high zeta potential will confer stability, i.e., the solution or dispersion will resist aggregation. When the potential is low, attraction exceeds repulsion and the dispersion will break and flocculate. So, colloids with high zeta potential (negative or positive) are electrically stabilized while colloids with low zeta potentials tend to coagulate or flocculate as outlined in the table.

| Zeta potential [mV] | Stability behavior of the colloid |
|---|---|
| from 0 to ±5, | Rapid coagulation or flocculation |
| from ±10 to ±30 | Incipient instability |
| from ±30 to ±40 | Moderate stability |
| from ±40 to ±60 | Good stability |
| more than ±61 | Excellent stability |

Although the ozonated fluid had a high Zeta potential of 60 indicating excellent stability for the ozonated fluid, limitations of the dynamic light scattering (DLS) tests on the ozonated fluid did not allow for good results in measuring the bubble size in nanometers. It is concluded that the low surface tension of the ozonated fluid clouds the DLS size measurement because the surface tension creates a sheet of ozonated fluid between the flow and the surface. The surface of the ozonated fluid behaves like an elastic film resulting in blocking the bubble size function of the DLS test. It is concluded that the bubble size is in the 100 to 500 nm range because of the high Zeta Potential.

A sample of ozonated fluid produced by the ozonated liquid dispensing unit 12 was further analyzed using a Nanosight LM10-HSGT nano-particle visualization device, which employs the Nanoparticle Tracking Analysis technique as defined in ASTM 2834-12. With this device, individual particles, i.e., the ozone nanobubbles in the ozonated fluid, are visualized down to approximately 10 nanometer in diameter. The device is not imaging the ozone nanobubbles at this size scale, i.e., no structural or shape information is available. Instead, the ozone nanobubbles are being visualized through the light that the particles scatter.

The concentration of particles for the sample was within the measurement range of the device and no dilution or other sample treatment was required. In this case, the "particles" are the nanobubbles of ozone, which scatter light and undergo Brownian motion in the same manner as a solid particle.

Figure 21:
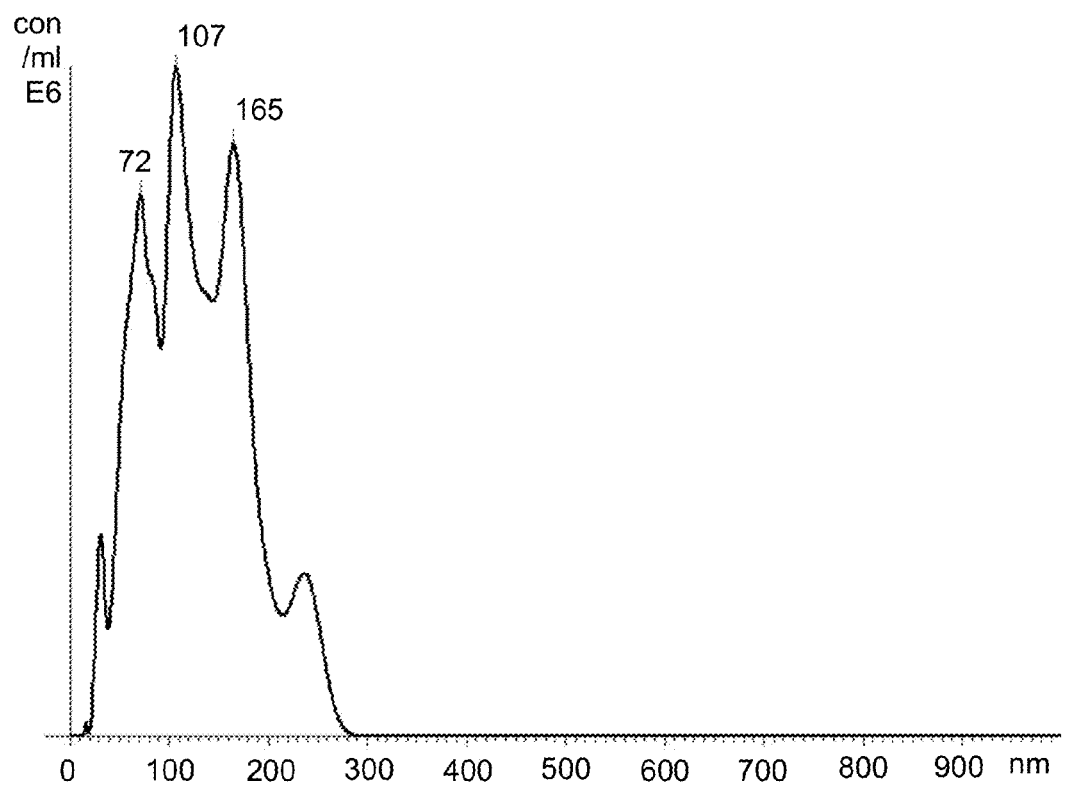
FIG. 21 is a graph showing the size distribution of nanobubbles in the ozonated fluid.

The sample of ozonated fluid showed a range of the ozone nanobubbles with a lower size limit around approximately 30 nm and a tail of the larger sizes up to approximately 300 nm. A graph showing the results is shown in FIG. 21. The results are also shown in the table below:

| Mode Size (nm) | D10 | D50 | D90 | Concentration (×10⁸ particles/ml) |
|---|---|---|---|---|
| 107 | 60 | 124 | 203 | 2.17 |

The analysis of the ozonated fluid showed that 10% of the ozone nanobubbles had a diameter less than 60 nanometers, 50% of the ozone nanobubbles had a diameter less than 124 nanometers, and 90% of the ozone nanobubbles had a diameter less than 203 nanometers. The analysis showed a mode size of 107 nanometers. No ozone nanobubbles having a diameter greater than 300 nanometers were found present in the ozonated fluid. As such, the ozonated fluid from the ozonated liquid dispensing unit 12 contained ozone nanobubbles having a diameter of approximately 30 nanometers to approximately 300 nanometers. The ozonated fluid from the ozonated liquid dispensing unit 12 contained only ozone nanobubbles having a diameter less than approximately 300 nanometers.

During the analysis, 300 μl of the ozonated fluid from the ozonated liquid dispensing unit 12 was introduced into the sample cell of the NanoSight LM10-HSGT using a 1 ml disposable syringe and visualized using a conventional optical microscope (×20 long working distance objective 0.40 NA) fitted with a scientific video camera (Hamamatsu CMOS). Images were collected directly to the hard drive as *.avi files with no further image processing.

The NanoSight LM10-HSGT uses a 532 nm, 50 mW laser to pass a laser beam through a prism-edged optical flat, the refractive index of which is such that the beam refracts at the interface between the flat and a liquid layer of the ozonated fluid placed above it. Due to the refraction, the beam compresses to a low profile, intense illumination region in which nanoparticles present in the liquid film can be easily visualized via the microscope. Mounted on a C mount, the CMOS camera, operating at 30 frames per second, is used to capture a video field of view approximately 100 μm×80 μm.

Figure 22:
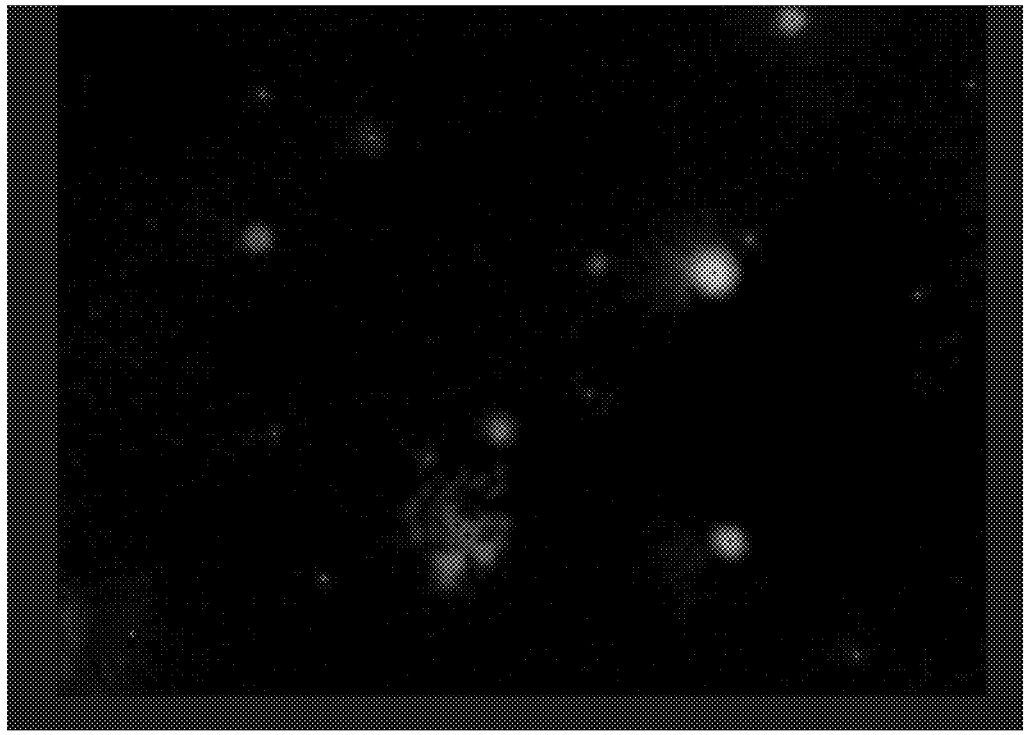
FIG. 22 is an image of the light scattering of the nanobubbles in the ozonated fluid.

Particles in the scattering volume are seen moving rapidly under Brownian motion. A software program simultaneously identifies and tracks the center of each particle on a frame-by-frame basis throughout the length of the video. A sample image from the video is shown as FIG. 22. The image is not a direct image of the ozone nanobubbles themselves, instead the image shows the light scattered by the ozone nanobubbles.

The average distance each particle moves in x and y in the image is automatically calculated, from which the diffusion coefficient (Dt) and hence sphere-equivalent, hydrodynamic diameter (d) can be determined using the Stokes-Einstein equation:

$$Dt = \frac{K_B T}{3\pi \eta d}$$

where $K_B$ is Boltzmann's constant, T is temperature and η is viscosity.

The scattering intensity of a particle is dependent upon its size (with larger particles scattering more light) and also its refractive index. The Brownian motion however, is dependent only upon the particle size, solvent viscosity and temperature (and is absolutely independent of particle density) and therefore provides an absolute measure of particle size, with smaller particles having a more exaggerated motion.

The intensity or brightness of the particles in the image may not necessarily indicate the presence of larger particles since the intensity of the particles may be associated with the refractive index of the particle. The video image, however, may be used to qualitatively assess the size of the particle both by the intensity and its Brownian motion (with the Brownian motion only being used to size the particle).

Those skilled in the art will appreciate that variations from the specific embodiments disclosed above are contemplated by the invention. The invention should not be restricted to the above embodiments, but should be measured by the following claims.

What is claimed:

1. An ozonated liquid dispensing unit, comprising:
   a liquid input port to receive water into the ozonated liquid dispensing unit from a water supply;
   a first dielectric cell to produce ozone gas;
   the first dielectric cell comprising an output trap connected to an output end of the first dielectric cell;
   a second dielectric cell for producing the ozone gas;
   the output trap of the first dielectric cell in communication with an input trap of the second dielectric cell for supplying the second dielectric cell with a supply gas comprising ozone gas generated from the first dielectric cell, and the second dielectric cell produces additional ozone gas from the supply gas;
   an injector in fluidic communication with the liquid input port;
   the injector in supply communication with the second dielectric cell for receiving the ozone gas from the first and second dielectric cells, wherein the injector mixes the ozone gas from the first and second dielectric cells with the water from the liquid input port to produce an ozonated liquid;
   a reaction vessel, the reaction vessel comprising a housing, the housing defining an interior; a first end of the housing comprising an entry port for the ozonated liquid; a second end of the housing comprising an exit port for the ozonated liquid; a conical member positioned in the interior of the housing between the entry port and the exit port; and,
   a liquid output port to discharge the ozonated liquid from the ozonated liquid dispensing unit.

2. The ozonated liquid dispensing unit according to claim 1, wherein the liquid output port is in fluidic communication with a sprayer, a distributor, an applicator, or other fluidic system.

3. The ozonated liquid dispensing unit according to claim 1, wherein the conical member is positioned generally centrally in the housing and the conical member is positioned generally vertically aligned with respect to a length of the housing.

4. An ozonated liquid dispensing unit, comprising:
   a liquid input port to receive water into the ozonated liquid dispensing unit from a water supply;
   a first dielectric cell to produce ozone gas;
   the first dielectric cell comprising an output trap connected to an output end of the first dielectric cell;
   a second dielectric cell for producing the ozone gas;
   the output trap of the first dielectric cell in communication with an input trap of the second dielectric cell for supplying the second dielectric cell with a supply gas comprising ozone gas generated from the first dielectric cell, and the second dielectric cell produces additional ozone gas from the supply gas;

an injector in fluidic communication with the liquid input port;

the injector in supply communication with the second dielectric cell for receiving the ozone gas from the first and second dielectric cells, wherein the injector mixes the ozone gas from the first and second dielectric cells with the water from the liquid input port to produce an ozonated liquid;

a reaction vessel, the reaction vessel comprising a housing, the housing defining an interior; a first end comprising an entry port for the ozonated liquid; a second end comprising an exit port for the ozonated liquid; a cone positioned in the interior of the housing between the entry port and the exit port; and, a liquid output port to discharge the ozonated liquid from the ozonated liquid dispensing unit.

5. The ozonated liquid dispensing unit according to claim 4, wherein the ozonated liquid discharged by the ozonated liquid dispensing unit contains ozone in nanobubbles having a diameter of 300 nanometers or less.

6. The ozonated liquid dispensing unit according to claim 4, wherein the ozonated liquid discharged by the ozonated liquid dispensing unit only contains ozone bubbles having a diameter less than approximately 300 nanometers.

7. The ozonated liquid dispensing unit according to claim 4, wherein the cone is positioned generally centrally in the housing and the cone is positioned generally vertically aligned with respect to a length of the housing.

8. The ozonated liquid dispensing unit according to claim 4, wherein the liquid output port is in fluidic communication with a sprayer, a distributor, an applicator, or other fluidic system.

9. The ozonated liquid dispensing unit according to claim 4, further comprising a faucet or sprayer in fluidic communication with the liquid output port, and actuation of the faucet or sprayer results in liquid flow in the ozonated liquid dispensing unit that activates the first dielectric cell and the second dielectric cell.

10. The ozonated liquid dispensing unit according to claim 4, further comprising an annular fluid passage between the cone and an inner surface of the housing, wherein the annular fluid passage fluidly connects the entry port and the exit port with the interior.

11. An ozonated liquid dispensing unit, comprising:
a liquid input port to receive water into the ozonated liquid dispensing unit from a water supply;
an ozone gas generator to produce ozone gas from ambient air;
an injector in fluidic communication with the liquid input port to receive the water;
the injector in supply communication with the ozone gas generator for receiving the ozone gas from ozone gas generator, wherein the injector mixes the ozone gas from the ozone gas generator with the water from the liquid input port to produce an ozonated liquid; and
a reaction vessel, the reaction vessel comprising a housing, the housing defining an interior; a first end comprising an entry port for the ozonated liquid; a second end comprising an exit port for the ozonated liquid; a cone positioned in the interior of the housing between the entry port and the exit port.

12. The ozonated liquid dispensing unit according to claim 11, wherein the exit port is in fluidic communication with a sprayer, a distributor, an applicator, or other fluidic system.

13. The ozonated liquid dispensing unit according to claim 11, wherein the cone is positioned generally centrally in the housing and the cone is positioned generally vertically aligned with respect to a length of the housing.

14. An ozonated liquid dispensing unit, comprising:
a liquid input port to receive water into the ozonated liquid dispensing unit from a water supply;
an ozone gas generator to produce ozone gas from ambient air;
an injector in fluidic communication with the liquid input port;
the injector in supply communication with the ozone gas generator for receiving the ozone gas from ozone gas generator, wherein the injector mixes the ozone gas from a first and second dielectric cells of the ozone gas generator with the water from the liquid input port to produce an ozonated liquid; and,
a reaction vessel, the reaction vessel comprising a housing, the housing having a generally cylindrical shape; the housing defining an interior; the housing comprising a first end comprising an entry port for the ozonated liquid, and a second end comprising an exit port for the ozonated liquid; a contact member is positioned in the interior of the housing between the entry port and the exit port to further mix the ozonated liquid, an annular fluid passage is between the contact member and an inner surface of the housing, wherein the annular fluid passage fluidly connects the entry port and the exit port with the interior of the housing.

15. The ozonated liquid dispensing unit according to claim 14, wherein the first end is inserted into the housing, and the second end is inserted into the housing.

16. The ozonated liquid dispensing unit according to claim 14, wherein the housing includes a first opening and a second opening, the first end includes a first rim portion and a first insert portion, and the first end includes a first central opening that forms the entry point and allows the ozonated liquid to enter the housing; and the second end includes a second rim portion and a second insert portion, and the second end has a second central opening that forms the exit port and allows the ozonated liquid to exit from the housing; and the first insert portion fits into the first opening of the housing to connect the first end to the housing, and the second insert portion fits into the second opening of the housing to connect the second end to the housing.

17. The ozonated liquid dispensing unit according to claim 14, wherein the contact member includes a plurality of ridges or steps.

18. The ozonated liquid dispensing unit according to claim 14, wherein the ozonated liquid discharged by the ozonated liquid dispensing unit contains ozone in nanobubbles having a diameter of 300 nanometers or less.

19. The ozonated liquid dispensing unit according to claim 14, wherein the exit port is in fluidic communication with a sprayer, a distributor, an applicator, or other fluidic system.

20. The ozonated liquid dispensing unit according to claim 14, wherein the contact member is positioned generally centrally in the housing and the contact member is positioned generally vertically aligned with respect to a length of the housing.

21. An ozonated liquid dispensing unit, comprising:
a liquid input port to receive water into the ozonated liquid dispensing unit from a water supply;
an ozone gas generator to produce ozone gas from ambient air;

an injector in fluidic communication with the liquid input port;

the injector in supply communication with the ozone gas generator for receiving the ozone gas from ozone gas generator, wherein the injector mixes the ozone gas from a first and second dielectric cells of the ozone gas generator with the water from the liquid input port to produce an ozonated liquid; and, a reaction vessel, the reaction vessel comprising a housing, the housing having a generally cylindrical shape, the housing defining an interior, the housing have a first opening and second opening; the housing comprising a first end, the first end including a first rim portion and a first insert portion, and the first end including a first central opening that allows the ozonated liquid to enter the housing; the housing comprising a second end, the second end including a second rim portion and a second insert portion, and the second end has a second central opening that allows the ozonated liquid to exit from the housing; the first insert portion fits into the first opening of the housing to connect the first end to the housing, and the second insert portion fits into the second opening of the housing to connect the second end to the housing; and, a contact member is in the interior of the housing to further mix the ozonated liquid as the ozonated liquid passes through the reaction vessel.

22. The ozonated liquid dispensing unit according to claim 21, wherein the second central opening is in fluidic communication with a sprayer, a distributor, an applicator, or other fluidic system.

23. The ozonated liquid dispensing unit according to claim 21, wherein the contact member is positioned generally centrally in the housing and the contact member is positioned generally vertically aligned with respect to a length of the housing.

* * * * *